US007993859B2

(12) United States Patent
Des Rosiers et al.

(10) Patent No.: US 7,993,859 B2
(45) Date of Patent: Aug. 9, 2011

(54) METHOD FOR QUANTIFYING OXIDATIVE STRESS CAUSED BY DIFFERENT BIOLOGICAL PATHWAYS

(75) Inventors: Christine Des Rosiers, Montreal (CA); Jean-Francois Lesgards, Marseille (FR); Jean-Claude Tardif, Laval (CA)

(73) Assignee: Institut de Cardiologie de Montreal, Montreal (CA)

( * ) Notice: Subject to any disclaimer, the term of this patent is extended or adjusted under 35 U.S.C. 154(b) by 0 days.

(21) Appl. No.: 12/832,176

(22) Filed: Jul. 8, 2010

(65) Prior Publication Data

US 2010/0330683 A1 Dec. 30, 2010

Related U.S. Application Data

(63) Continuation-in-part of application No. 12/083,473, filed as application No. PCT/CA2006/001696 on Oct. 14, 2006.

(60) Provisional application No. 60/726,233, filed on Oct. 14, 2005, provisional application No. 60/809,336, filed on May 31, 2006, provisional application No. 61/213,733, filed on Jul. 8, 2009.

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50

(58) Field of Classification Search ........................ None
See application file for complete search history.

(56) References Cited

OTHER PUBLICATIONS

Veronneau, M. et al Quantitative Gas Chromatographic—I Mass Spectrometr C Rad C. Biol. Med 33:1380-1388; Aug. 2002.*
Crabb, John W. et al Hydroxynonenal Inactives Cathepsin B. Protein Science 2002 11:831-840 Dec. 2001 USA.*

* cited by examiner

*Primary Examiner* — Lisa Cook
(74) *Attorney, Agent, or Firm* — Dowell & Dowell, P.C.

(57) ABSTRACT

The present invention relates to methods for detecting a oxidative stress in a biological sample, methods of determining a cumulative record of oxidative injury, and methods of diagnosing diseases of aging, such as cardiovascular diseases, based on the presence or absence of a biomarker or a component thereof. The present invention also relates to a kit for detecting oxidative stress in a biological sample comprising a stabilizing reactant and an antibody. In some embodiments of the invention, the biomarker of oxidative stress is selected from an aldehyde-protein adduct and an aldehyde metabolite-protein adduct, and the proposed method further comprises measuring separately for the same protein biomarkers of oxydative stress formed with different amino acids of the protein.

2 Claims, 13 Drawing Sheets

- m/z 257: *(light isotopic impurities from $NaB^2H_4$ and $[^2H_{11}]DHN$)*
- m/z 258: $[^2H]DHN$ *(sulfur-bound HNE reduced with $NaB^2H_4$)*
- m/z 268: $[^2H_{11}]DHN$ *(internal standard)*

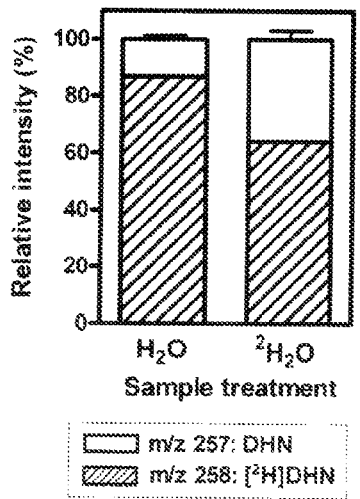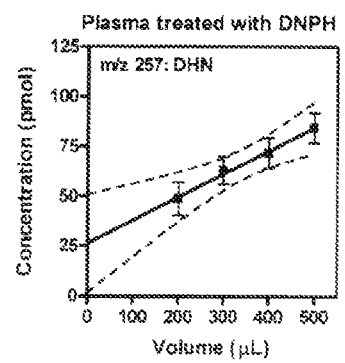
FIGURE 17
FIGURE 19
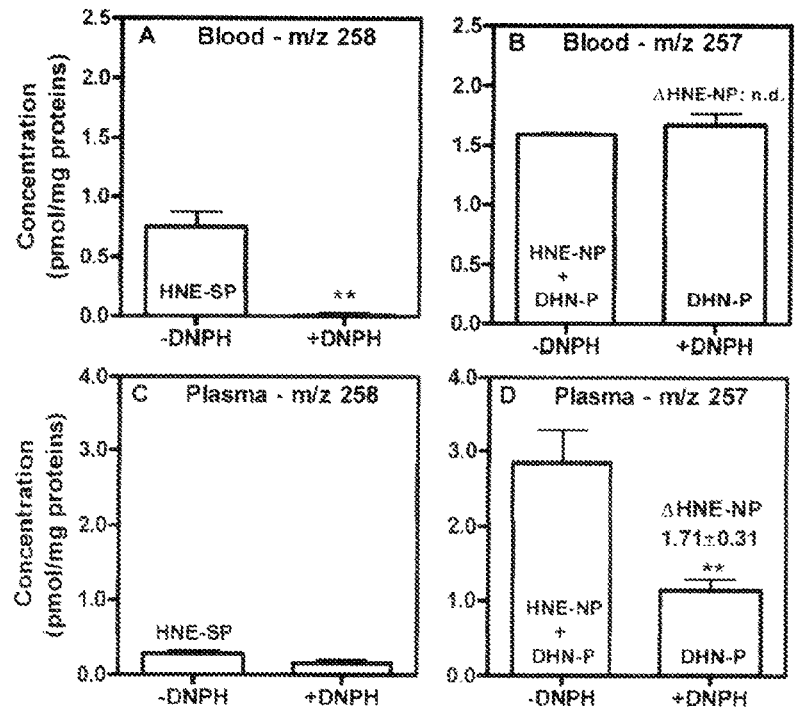
FIGURE 20

METHOD FOR QUANTIFYING OXIDATIVE STRESS CAUSED BY DIFFERENT BIOLOGICAL PATHWAYS

The present application is a continuation in part of U.S. patent application Ser. No. 12/083,473 filed on Apr. 14, 2008, still pending, which is a US National phase of PCT Patent Application Serial Number PCT/CA2006/001696 filed on Oct. 14, 2006, which claimed priority from U.S. Provisional Patent Applications Ser. No. 60/726,233 filed Oct. 14, 2005 and Ser. No. 60/809,336 filed May 30, 2006. This application also claims priority from U.S. Provisional Patent Applications Ser. No. 61/213,733 filed on Jul. 8, 2009. The disclosures of all the previously mentioned patent applications are hereby incorporated by reference in their entirety.

FIELD OF THE INVENTION

The present invention relates to methods for detecting an oxidative stress in a biological sample, methods of determining a cumulative record of oxidative injury, and methods of diagnosing diseases of aging, such as cardiovascular diseases, based on the presence or absence of a biomarker or a component thereof, and to methods for quantifying oxidative stress caused by different biological pathways. The present invention also relates to a kit for detecting oxidative stress in a biological sample comprising a stabilizing reactant and an antibody.

BACKGROUND OF THE INVENTION

Increasing evidence supports the involvement of reactive carbonyl compounds, particularly α,β-unsaturated aldehydes generated endogenously during lipid peroxidation of polyunsaturated fatty acids, in the onset and progression of cardiovascular diseases [1,2]. One of the most toxic aldehydes is 4-hydroxy-2-nonenal (HNE). HNE represents >95% of the total unsaturated aldehydes produced during in vitro microsomal lipid peroxidation and it is generated in 100-fold excess over malondialdehyde during oxidation of arachidonic acid [3,4]. The Michael addition of carbon 3 of HNE to the sulfhydryl group of cysteine, ε-amino group of lysine and imidazole function of histidine has been well documented and the order of reactivity towards these amino acid residues of proteins was found to be: cysteine>>histidine>lysine [5]. Several protein targets for HNE binding have been identified such as mitochondrial NADP-linked isocitrate dehydrogenase, cytochrome C oxidase, hemoproteins and more recently, fatty acid binding protein [1-7].

Protein-bound HNE (HNE-P) in biological matrices were first detected using an immunochemical approach in a variety of conditions associated with oxidative stress in both animals and humans (for e.g. atherosclerotic lesions) [8]. The use of monoclonal antibodies recognizing various HNE-derived epitopes has enable investigators to obtain data supporting HNE involvement in several pathological conditions such as atherosclerosis [9], Parkinson's disease [10], and diabetes [11]. Although HNE adducts have been detected in circulating proteins [12,13], immunochemical techniques do not easily lend themselves to quantitative assessments of these adducts in plasma and blood [14]. More recently, the analysis of HNE-P have been improved by matrix-assisted laser ionization and electrospray ionization mass spectrometry[1,15]. Some of these applications have proven their accuracy and sensitivity [16,17], but to the best of our knowledge, they have not yet been used for quantification and analyses of the bulk of HNE-P in biological fluids. However, this field is rapidly evolving and new approaches are being developed to circumvent current limitations (for a recent review see ref. [18]).

Meanwhile, several gas chromatography-mass spectrometry (GCMS) methods were developed for the determination of free HNE as pentafluorobenzyl oxime derivatives in blood plasma or LDL [19,20]. Requena et al. were the first to apply GCMS to the determination of HNE bound to lysine residues of proteins following reduction with NaBH4 and peptide hydrolysis under acidic conditions [21]. Recently, we developed and validated a quantitative GCMS method that enables the detection at the picomolar level of HNE-P in blood, plasma, as well as in other biological tissues [22,23]. The principle of this method is illustrated in FIG. 10 (left panel). Briefly, it involves reduction of HNE's free reactive carbonyl group to an inactive deuterated alcohol using NaB2H4. Then, the sample is treated with Raney nickel to cleave thioether linkages thus releasing [2H2]-1,4-dihydroxynonane (DHN), which is then converted to a t-butyldimethylsilyl (TBDMS) ether and analyzed by GCMS. Quantification is achieved using a deuterated internal standard [2H11]-1,4-dihydroxy-2-nonene, which is reduced to [2H11]1,4-dihydroxynonane ([2H11]DHN) by Raney nickel.

SUMMARY OF THE INVENTION

In summary, quantification of 4-hydroxy-2-nonenal (HNE) bound to circulating proteins may prove to be useful in evaluating the role of this bioactive lipoperoxidation by-product in the pathogenesis of various diseases. We developed previously a quantitative gas chromatography-mass spectrometry (GCMS) assay of total protein-bound HNE (HNE-P) in blood following reduction with $NaB^2H_4$ and cleavage with Raney nickel. While it has been assumed that Raney nickel cleaves only Michael adducts of HNE to cysteine via a thioether bond (HNE-SP), results from this study demonstrates that our GCMS method detects also with precision picomoles of HNE adducts via nitrogen residues (HNE-NP). Specifically, evidence was obtained using various study models, including polyamino acids consisting of cysteine, lysine and histidine, and a biologically-relevant molecule, albumin. Furthermore, we show that dinitrophenylhydrazine treatment prior to Raney nickel treatment can be used to discriminate and quantify the various HNE-P molecular species in plasma and blood samples from normal rats, which range between 0.15 and 3 pmol/mg protein or 10 to 600 nM. Interestingly, while HNE-SP predominated in whole blood, we detected HNE-NP only in plasma. Furthermore, we identified another significant MS signal, which we attribute to protein-bound 1,4-dihydroxynonane (DHN-P) presumably formed from the enzymatic reduction of HNE-SP. It is noteworthy that the distribution profile of all these species in plasma differed from that observed when physiologically-relevant concentrations of albumin and HNE were incubated in vitro. Beyond documenting the presence of various types of HNE-P in circulating proteins, our results emphasize the importance of enzymatic mechanisms in situ as a factor determining their distribution in the various blood compartments.

Treatment with Raney nickel, which involves a catalytic hydrogenation reaction that is known as "desulfurization", was previously shown to cleave only HNE-P via thioether linkages [24,25]. There is one report discussing the possibility that Raney nickel may also cleave carbon-nitrogen linkages [26], but to the best of our knowledge, this possibility has not been examined for HNE-P. Hence, one aim of this study was first to determine if our recently developed GCMS method detects Michael adducts of HNE with lysine and histidine residues. Using as our study model polyamino acids (PAA) consisting of lysine or histidine, or cysteine, we have found that our GCMS assay can detect HNE bound to lysine and histidine residues and that these adducts react differently from HNE-cysteine adducts to Raney nickel treatment. Thus, we also conducted additional experiments to explore the potential significance of our finding using biologically relevant molecule (albumin) and samples (blood and plasma).

In a first broad aspect, the invention relates to a method for detecting oxidative stress using a biological sample containing a biomarker of oxidative stress. The method includes obtaining a biological sample, chemically stabilizing the biomarker of oxidative stress to produce a stabilized biomarker of oxidative stress; and, after having stabilized the biomarker of oxidative stress, assessing the presence of the stabilized biomarker of oxidative stress in the sample.

Advantageously, the method allows to perform relatively complex and lengthy processes when assessing the presence of the biomarker while ensuring that levels of the biomarker inside the sample remain substantially constant during these processes.

In addition, the method is relatively easy to perform using standard laboratory procedures.

In some embodiments of the invention, the method may be performed using a kit which therefore allows to relatively effectively and simply perform the method in a relatively small number of relatively easily performed steps.

For more clarity, for the purpose of this document, the term biomarker of oxidative stress encompasses biomarkers of oxidative stress per se and biomarkers of oxidative stress-related events, such as for example and non-limitingly, biomarkers of oxidative stress-induced LPO events involved in aging and in the development and progression of cardiovascular diseases.

In some embodiments of the invention, the biomarker of oxidative stress is selected from an aldehyde-protein adduct and an aldehyde metabolite-protein adduct. For example, the metabolite-protein adduct is a metabolite-protein thioether adduct. In other examples, the metabolite is covalently bound to any suitable amino acid, such as histidine or lysine, among others, or to any other suitable substance.

In specific embodiments of the invention, the aldehyde includes 4-hydroxy-2,3-nonenal (HNE), 1,4-dihydroxynonene (DHN). In these two cases, in some embodiments of the invention, the measurable component may be selected from DHN and [$^2$H]DHN. In other embodiments the measurable component of the biomarker of oxidative stress is another metabolite produced by peroxidation of fatty acids, such as non-limitingly 4-hydroxynonenal, 4-oxononenal, 4-hydroxyhexenal and 4-oxohexenal.

In some embodiments, the quantity of the measurable component is measured using gas chromatography coupled to mass spectrometry.

In some embodiments of the invention, chemically stabilizing the biomarker in the sample includes reducing the aldehyde to its alcohol, for example by adding $NaB^2H_4NaBH_4$ or to the biological sample. In a variant of the embodiments, reducing the aldehyde to its alcohol comprises reducing HNE to DHN and/or reducing HNE to its deuterated alcohol [$^2$H]DHN.

In some embodiments of the invention, the biological sample contains molecules selected from HNE, HNE-protein adducts, DHN, DHN-protein adducts, metabolites of HNE, and combinations thereof.

In some embodiments of the invention, isolating the measurable component includes cleaving a protein linkage. For example, the step of cleaving a protein linkage comprises cleaving a protein thioether linkage using Raney nickel catalysis. In a specific example, the Raney nickel catalysis is conducted for about 5 to about 20 hours at a temperature of about 45° C. to about 60° C.

In some embodiments of the invention, the biological sample is selected from whole blood, blood derivatives, and combinations thereof, the blood derivatives being selected for example from plasma, albumin, and oxidized lipoprotein, among others.

In a second broad aspect, the invention relates to a method for detecting oxidative stress using a biological sample comprising obtaining a biological sample comprising a biomarker of oxidative stress; chemically stabilizing the biomarker in the sample; contacting the sample with an antibody that binds to the stabilized biomarker; and detecting the presence of the bound antibody in the sample.

In a third broad aspect, the invention relates to a method for determining a cumulative record of oxidative injury in a mammal over time, comprising: obtaining a first blood sample from a mammal at a first time point, wherein the blood sample comprises an aldehyde metabolite-protein adduct; detecting a level of oxidative stress in the first blood sample based on the quantity of the aldehyde metabolite; obtaining a second blood sample from a mammal at a second time point wherein the blood sample comprises an aldehyde metabolite-protein thioether adduct; detecting a level of oxidative stress in the second blood sample based on the quantity of the aldehyde metabolite; and determining a cumulative record of oxidative injury in the mammal using the quantities of aldehyde metabolite measured in the first and second blood samples.

In a fourth broad aspect, the invention relates to a method for assessing the risk of cardiovascular disease in a mammal, comprising: obtaining from a mammal a biological sample comprising HNE-protein adduct and DHN-protein adduct; measuring the quantities of HNE-protein adduct and DHN-protein adduct in the sample; determining a predetermined relationship between the HNE-protein adduct and the DHN-protein adduct; assessing the risk of cardiovascular disease in the mammal based on the predetermined relationship.

In a fifth broad aspect, the invention relates to a method for diagnosing a cardiovascular disease, or risk thereof, in a mammal, for example a human, comprising: obtaining from a mammal a biological sample comprising an aldehyde metabolite-protein adduct; measuring the quantity of the aldehyde metabolite-protein adduct in the sample; and diagnosing the mammal as having a cardiovascular disease, or risk thereof, if the quantities of aldehyde metabolite-protein thioether adduct present in the biological sample is greater than a predetermined threshold. For example, the cardiovascular disease or a risk factor thereof is selected from hypertension, insulin resistance, hyperglycemia, hyperlipidemia, diastolic dysfunction, fibrosis of the myocardium, and arrhythmia, cardiac hypertrophy and tachycardia. Also, for the purpose of the present specification, the term risk as it relates to cardiovascular diseases includes other diseases or conditions for which cardiovascular diseases are complications, such as diabetes, obesity, and metabolic syndrome.

In a sixth broad aspect, the invention relates to a method for diagnosing a cardiovascular disease, or risk thereof, in a mammal, comprising: obtaining from a mammal a biological sample comprising HNE-protein thioether adduct and DHN-protein thioether adduct; and diagnosing the mammal as having a cardiovascular disease, or risk thereof, if the ratio between the quantities of HNE-protein thioether adduct and DHN-protein thioether adduct is greater than a predetermined ratio.

In other embodiments of the invention, any other suitable relationship between the quantities of HNE-protein thioether adduct and DHN-protein thioether adduct is used to diagnose the cardiovascular disease or the risk thereof, such as for example a sum of these two quantities.

In a seventh broad aspect, the invention relates to a kit for detecting oxidative stress related events using a biological sample, wherein the biological sample is selected from whole blood and blood derivatives, and comprises an aldehyde, and the kit comprises: a stabilizing reactant for stabilizing the aldehyde to its alcohol; and an antibody that binds specifically to the stabilized alcohol. For example, the stabilizing reactant is suitable for converting the aldehyde to its alcohol.

In an eight broad aspect, the invention relates to a method of slowing or stopping cardiovascular disease progression in a human subject, comprising: diagnosing cardiovascular disease, or risk thereof, in a human subject according to the method of claim 28; and administering a predetermined treatment known to slow or stop cardiovascular disease progression. For example, the predetermined treatment comprises administering a therapeutically effective amount of Probucol, recommending an exercise program effective for slowing or stopping cardiovascular disease progression and administering a diet effective for slowing or stopping cardiovascular disease progression, among others In a ninth broad aspect, the invention relates to a method for determining a cumulative record of oxidative injury in a mammal over time, comprising: obtaining a blood sample from a mammal, wherein the blood sample comprises an aldehyde metabolite-protein adduct; detecting a level of oxidative stress using the blood sample based on the quantity of the aldehyde metabolite present in the blood sample; and determining a cumulative record of oxidative injury in the mammal using the quantities of aldehyde metabolite measured in blood samples and a predetermined reference quantity of the aldehyde metabolite.

In a tenth broad aspect, the invention relates to a method of assessing a response of cardiovascular disease progression to a predetermined treatment in a human subject, comprising: obtaining from a mammal a biological sample comprising an aldehyde metabolite-protein adduct; measuring the quantity of the aldehyde metabolite-protein adduct in the sample; and; assessing the response of the cardiovascular disease progression to the predetermined treatment on a basis of the measured quantity of the aldehyde metabolite-protein adduct in the sample.

In some embodiments of the invention, the proposed method quantifies oxidative stress caused by different biological pathways by measuring seperately HNE-protein adducts bound to cysteine, lysine and histidine.

Other objects, advantages and features of the present invention will become more apparent upon reading of the following non restrictive description of preferred embodiments thereof, given by way of example only with reference to the accompanying drawings.

BRIEF DESCRIPTION OF THE DRAWINGS

FIG. 17, in a bar chart, illustrates GCMS analysis of plasma samples treated with Raney nickel in H2O and 2H2O. Plasma samples (400 µL) were processed as described the Methods and shown in FIG. 10 except that at the Raney nickel step, samples were dissolved either in H2O or 2H2O. GCMS data are corrected for natural abundance intensity and expressed as % of the total GCMS signal at ions m/z 257 and 258. Values are means±SD of two experiments conducted in 3-5 replicate determinations (CV<10%). Note the increase in signal intensity at m/z 258 for samples treated with 2H2O;

FIG. 19, in an X-Y graph, illustrates a Calibration curve obtained for the GCMS assay of HNE-P at m/z 257 in increasing volume of plasma in the presence of DNPH. Samples for the various volumes were processed for analysis in triplicates. Data are reported as concentration, calculated using the internal standard of [2H11]DHN after correction for natural abundance in heavy isotopes. The regression line with 95% confidence interval is shown: slope=0.12±0.03, y-intercept=26±11; Pearson correlation coefficient r=0.996; p<0.004;

FIG. 20, in bar charts, illustrates GCMS analysis of various protein-bound HNE and DHN species in blood and plasma rat samples with or without treatment with DNPH. Whole blood and plasma samples were processed in the presence of DNPH for the GCMS analysis of DHN released from the various protein (P) adducts: protein-bound HNE via cysteine (HNE-P) or histidine/lysine residues (HNE-NP), and protein-bound DHN (DHN-P). Data shown are expressed as concentrations, which were calculated for the GCMS signal at m/z 258 (panels A & C) and m/z 257 (panels B & D), corrected for natural abundance in heavy isotopes, using the internal standard [2H11]DHN. There are means±SE of 7 rat plasma or blood samples. **p<0.01; +DNPH vs.-DNPH. n.d.: not detected; Δ: difference in concentration at m/z 257±DNPH; and

DETAILED DESCRIPTION

Figure 1:
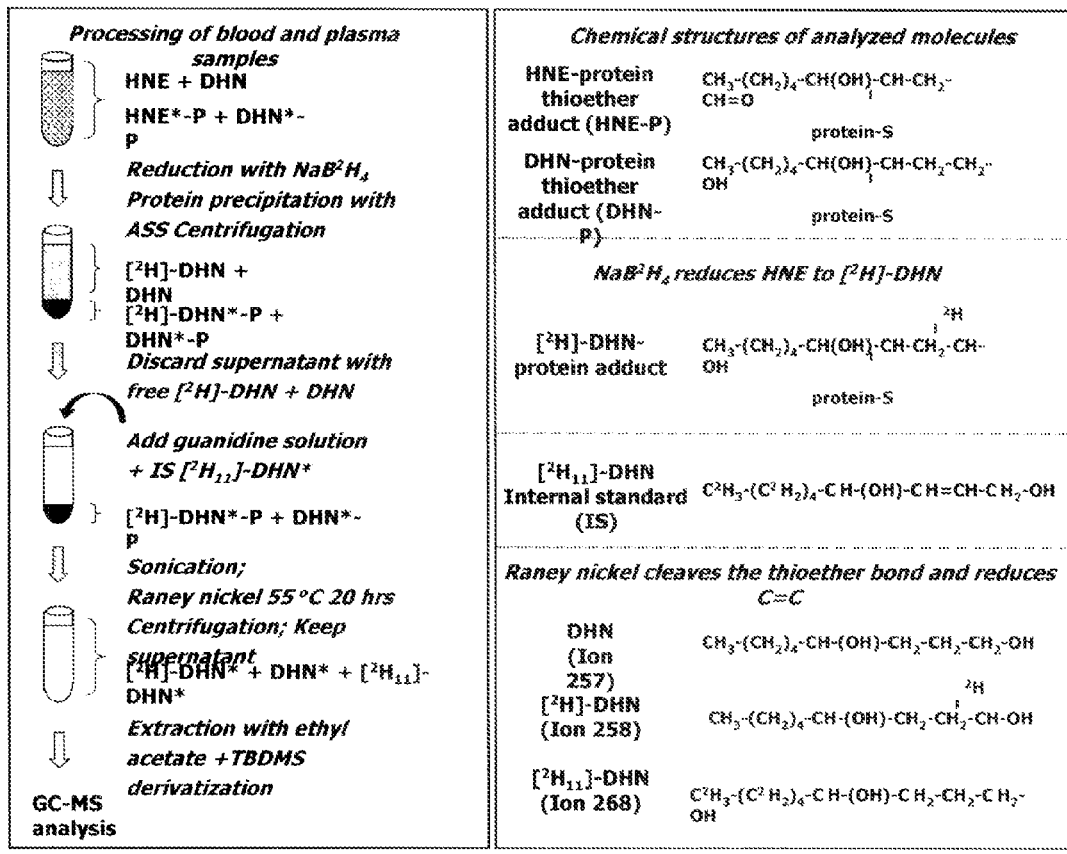
FIG. 1, in a schematic view, illustrates an overview of an experimental procedure to quantify HNE and its metabolite DHN bound to a protein via thioether linkage in blood by isotope dilution GCMS in accordance with an embodiment of the present invention, the symbol * indicating the measured molecules.

The following examples illustrate the above-mentioned method for detecting oxidative stress in a biological sample, and show that this method may be performed, for example, on an aldehyde produced through peroxidation of fatty acids. In some variants of these embodiments, stabilizing the biomarker of oxidative stress includes converting the aldehyde to its alcohol.

In some embodiments of the invention, the sample includes whole blood or a blood derivative. As used herein, the term "blood" generally refers to whole blood and blood derivatives (e.g., plasma, albumin, etc.) These samples are relatively easy to obtain and have been found to contain suitable biomarkers of oxidative stress for use in the present invention.

Some example of suitable biomarker of oxidative stress for which the proposed method are useful include: 4-hydroxy-2,3-nonenal (HNE), 1,4-dihydroxynonene (DHN), 4-hydroxynonenal, 4-oxononenal, 4-hydroxyhexenal and 4-oxohexenal. In some embodiments of the invention, these biomarkers are in the form of an aldehyde metabolite-protein adduct, such as an aldehyde metabolite-protein thioether adduct. In some variants of these embodiments, the method includes cliving the aldehyde metabolite from the aldehyde metabolite-protein thioether adduct and afterwards extracting the aldehyde metabolite-protein thioether adduct from the biological sample.

In some embodiments of the invention, a suitable analytical technique, such as for example gas chromatography, is used to assess the presence of the biomarker of oxidative stress in the sample, and in some embodiments to measure or quantify a quantity of the biomarker of oxidative stress present in the sample. In these embodiments, some variants allow quantification of aldehyde metabolite-protein adducts bound via different amino acids, which are indicative of different pathways of oxidative stress. Indeed, different physiological pathways resulting from oxidative stress may, in some cases, affect differently the manner in which the aldehyde metabolite-protein adducts are created, which is reflected in the different amino acids through which the aldehyde metabolite-protein adducts are created. In other embodiments, assessing the presence of the biomarker of oxidative stress in the sample includes contacting the sample with an antibody which binds to the stabilized biomarker of oxidative stress under conditions which allow binding of the stabilized biomarker of oxidative stress to the antibody and detecting the presence of bound antibody in the sample.

Some example of suitable biomarker of oxidative stress for which the proposed method are useful include: 4-hydroxy-2,3-nonenal (HNE), 1,4-dihydroxynonene (DHN), 4-hydroxynonenal, 4-oxononenal, 4-hydroxyhexenal and 4-oxohexenal. In some embodiments of the invention, these biomarkers are in the form of an aldehyde metabolite-protein adduct, such as an aldehyde metabolite-protein thioether adduct. In some variants of these embodiments, the method includes cliving the aldehyde metabolite from the aldehyde metabolite-protein thioether adduct and afterwards extracting the aldehyde metabolite-protein thioether adduct from the biological sample.

In some embodiments of the invention, a suitable analytical technique, such as for example gas chromatography, is used to assess the presence of the biomarker of oxidative stress in the sample, and in some embodiments to measure or quantify a quantity of the biomarker of oxidative stress present in the sample. In other embodiments, assessing the presence of the biomarker of oxidative stress in the sample includes contacting the sample with an antibody which binds to the stabilized biomarker of oxidative stress under conditions which allow binding of the stabilized biomarker of oxidative stress to the antibody and detecting the presence of bound antibody in the sample.

The present invention also relates to a method of slowing or stopping cardiovascular disease progression in a mammal (preferably, a human) by diagnosing cardiovascular disease, or risk thereof, according to the methods described herein, and administering a predetermined treatment known to slow or stop cardiovascular disease progression. Examples of suitable such predetermined treatments include administering a therapeutically effective amount of Probucol, recommending an exercise program effective for slowing or stopping cardiovascular disease progression, and administering a diet effective for slowing or stopping cardiovascular disease progression and administering a therapeutically effective amount of Probucol.

ANIMAL MODEL EXAMPLES

The present invention is next described by means of the following examples that were performed using animal models. The use of these and other examples anywhere in the specification is illustrative only, and in no way limits the scope and meaning of the invention or of any exemplified form. Likewise, the invention is not limited to any particular preferred embodiments described herein. Indeed, modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Experiments were performed to assess if circulating levels of HNE-protein adducts (i) can be assessed with precision by GCMS and (ii) vary with disease progression and aging in a model of cardiomyopathy that displays enhanced oxidative stress, namely the spontaneously hypertensive rats (SHR).

While they were performed in rats, the experiments described herein are expected to be predictive of biological effects in humans or other mammals and/or to serve as models for use of the present invention in humans or other mammals. These examples illustrate the above-mentioned methods, such as detecting oxidative stress in a biological sample, determining a cumulative record of oxidative injury, diagnosing cardiovascular diseases, and characterizing cardiovascular disease activity.

Example 1

An experiment was performed in order to quantify HNE and its inactive metabolite, 1,4-dihydroxynonene (DHN), bound to thiol protein adducts following treatment with $NaB^2H_4$ and Raney nickel. Levels of these adducts were measured in blood and plasma collected from SHR and control Wistar rats at 7, 15, 22 and 30 weeks of age. Levels of protein-bound HNE, which were quantitated with relatively good precision in the nanomolar range in blood, but not in plasma, were significantly increased by disease (SHR) and age ($p<0.0001$ for both). Compared to Wistar rats, SHR showed greater blood levels of HNE-protein adducts at 22 and 30 weeks. Levels of protein-bound DHN, which were detected in blood and in plasma, were not affected by disease or age. Collectively, the results of this study conducted in an animal model of cardiomyopathy demonstrate that changes in blood HNE-protein thioether adducts with disease progression and aging can be assessed with good precision by the described GCMS method. It is expected that this method will be useful in evaluating the occurrence and impact of oxidative stress-related events involving bioactive HNE in diseases of aging, such as cardiovascular diseases, particularly in humans.

Example 2

Another experiment was performed to assess the role of 4-hydroxynonenal (HNE) in oxidative-stress related diseases. Further to the finding of high circulating HNE-protein thioether adducts (HNE-P) in spontaneously hypertensive rats (SHR), this study aimed at correlating HNE-P with cardiac function and testing the impact of antioxidant therapy.

The lipoperoxidation inhibitor Probucol (10 mg/kg/day) or vehicle (corn oil) were administered daily (i.p.) for 4 weeks in 18-week-old SHR (9 rats/group). Cardiac functions were assessed by echocardiography and HNE-P by GCMS.

Diastolic dysfunction worsened in SHR receiving vehicle as reflected by changes ($p<0.05$) in indexes of left ventricular relaxation (increased isovolumic relaxation time) and compliance (increased E wave deceleration rate, EDR). Higher circulating HNE-P correlated with diastolic dysfunction (EDR: $R2=0.518$; $p<0.001$) and heart rate ($R2=0.225$; $p<0.05$). Probucol prevented the deterioration of diastolic function, while lowering the mean and median of circulating HNE-P by 21% and 35%, respectively. Collectively, these results support a role for HNE in the pathophysiological events linked to disease progression in SHR.

Example 3

In this next example, a method using quantitative GCMS assay of protein-bound HNE in myocardial tissues [1A] was modified to enable precise and reproducible serial assessments of the small level of these adducts in blood samples. Specifically, this method quantified HNE as well as its inactive metabolite, DHN, bound to thiol proteins. However, in alternative embodiments of the invention, oxidative stress may be quantified using any other suitable substance, such as for example any other aldehyde metabolite produced by the peroxidation of fatty acids. HNE-protein thioether adducts and DHN-protein thioether adducts are considered representative of the classes of aldehyde-protein adducts and aldehyde metabolite-protein adducts.

In summary, the method involves (i) stabilisation of HNE through reduction to its deuterated alcohol [$^2$H]DHN, (ii) treatment with Raney Nickel to cleave thioether linkages, releasing protein-bound DHN and [$^2$H]DHN (HNE), and (iii) the use of a deuterated internal standard, [$^2$H$_{11}$]DHN that enables positive identification and quantification of the DHN chromatographic peak. As used herein, the term "[$^2$H]DHN (HNE)" refers to the stabilized deuterated alcohol of HNE. Using the modified method, the levels of circulating protein-bound HNE and DHN were assessed in 7, 15, 22 and 30-week-old spontaneously hypertensive rats (SHR) and control Wistar rats.

The SHR is a well-established model of genetic hypertension, which displays enhanced oxidative stress that responds to antioxidant treatment [2A,3A] as early as 4 weeks of age in the vascular wall and in the myocardium, [4A-6A] including accumulation of HNE-protein adducts [7A]. Collectively, the results of this example demonstrate an increase in circulating HNE, but not DHN, bound to protein thiols with disease progression and aging in SHR. These results suggest the potential of these adducts as a circulating marker of oxidative stress-related events involving bioactive HNE.

Materials and Methods (Example 3)

Chemicals

Chemical, Raney Nickel, 2,6-tert-butyl-4-methylphenol (BHT), organic solvents and acids were obtained from Laboratory MAT (Quebec, Quebec, Canada), Sigma Chemical Co (St-Louis, Mo., USA), Bio-Rad (Hercules, Calif., USA) and Fisher Scientific (Nepean, Ontario, Canada) respectively. Anhydrous ammonia gas for chemical ionization (CI; 99.99% minimal purity) and helium gas (UHP) were obtained from Matheson Gas Product Canada (Montreal, Quebec, Canada). Unlabeled HNE was purchased from BIOMOL (Plymouth Meeting, Pa., USA) and the derivatization agent N-methyl-N-(tert-butyldimethylsilyl)-tri-fluoroacetamide (TBDMS) from Regis Chemical (Morton Grove, Ill., USA). Sodium borodeuteride (NaB$^2$H$_4$) and trans-4-hydroxy-2-nonenal-([5, 5,6,6,7,7,8,8,9,9,9-2H11] ([$^2$H$_{11}$]HNE) diethyl acetal were supplied by Cambridge Isotope (Andover, Mass., USA) and CDN Isotope (Pointe-Claire, Quebec, Canada). Publication [18] provides details about the preparation of stock solutions of [$^2$H$_{11}$]DHN and DHN, as well as determination of their concentration by measurement of HNE solution absorbance at 223 nm, prior to reduction with NaBH4. All aqueous solutions were prepared with water purified by milli-Q system (Millipore, St-Laurent, Quebec, Canada). All other reagents were of analytical grade.

Animals and Sample Collection

Animal experiments were approved by the local animal care committee in compliance with the guidelines of the Canadian Council on Animal Care. Rats were housed for at least 7 days in a 12-h light/12-h dark cycle facility with unlimited access to water and standard chow prior to sacrifice. Male SHR and age-matched control Wistar rats (Charles River, St-Constant, Quebec, Canada) were sacrificed at 7 (n=11), 15 (n=13), 22 (n=8) and 30 (n=8) weeks of age. Body weights at sacrifice were, respectively, 187±13, 332±22, 375±9 and 406±15 g for SHR and 239±28, 442±31, 533±32 and 612±15 g for Wistar rats. Blood was collected under sodium pentobarbital anesthesia (65 mg/g, intraperitoneal; MTC Pharmaceuticals) by cardiac puncture with a 10-ml syringe pre-coated with EDTA (10.8 mg) and BHT (0.0496 mg). A sample of whole blood (500 μA was immediately frozen in liquid nitrogen. The remaining volume was centrifuged at 1,500 g for 10 min and the collected plasma sample was also immediately frozen in liquid nitrogen. All samples were kept at −80° C. until analysis.

Analytical Procedures

The procedure for sample preparation and GCMS analysis of HNE- and DHN-protein adducts in blood and plasma is outlined in FIG. 1. The previously described method for detecting protein-bound HNE in myocardial tissues [1A] was modified to increase its sensitivity 20-fold to enable detection of the lower quantity of protein-derived HNE and DHN found in blood and plasma samples, as well as to improve its reproducibility and ruggedness. Routinely, blood and plasma samples (400 μA were individually mixed with 1 ml of cold buffer (pH 7.0) containing 39 mM Hepes, 0.4 mM EDTA and 0.9 mM BHT to minimize lipid peroxidation during processing, immediately treated with 200 μl 1 M NaB$^2$H$_4$ to reduce HNE to its chemically stable alcohol derivative [$^2$H]DHN, and left on ice for 30 min.

Then, proteins were precipitated by addition of saturated sulfosalicylic acid (final concentration 8% (v/v)). After 30 min on ice, samples were centrifuged at 5,000 g for 45 min. The protein pellets were washed with 3 ml methanol:chloroform (2:1) to remove lipids and with water three times, resuspended into 500 μl of solution containing 8 M guanidine, 13 mM Tris (pH 7.2) and 133 mM EDTA, and spiked with 0.1 nmol of deuterated internal standard [$^2$H$_{11}$] DHN. Solutions were sonicated (3×20 sec) to optimize protein dissolution, and 1 ml of water was added before treatment with 2.5 g of Raney Nickel catalysis for 20 h at 55° C. Since this treatment cleaves thioether linkages and reduces C═C bonds, free saturated derivative of [$^2$H]DHN and DHN are released into solutions and are subsequently processed for GCMS analysis. Hence, following centrifugation, twice at 1700 g for 3 min at room temperature, the aqueous supernatants were brought to pH<2 with concentrated HCl, saturated with sodium chloride and extracted two times with 10 ml of ethyl acetate by vortexing 3 min. The extracts were evaporated under nitrogen and the residues were treated with 50 ml of TBDMS. For optimal derivatization, samples were heated during 4 hours at 90° C. Protein determination was achieved by the Bradford assay [28] using bovine serum albumin (Fraction V, Sigma) as standard. The recovery of proteins after precipitation with saturated sulfosalicylic acid was evaluated to be >99% based on protein determination in the supernatant.

GCMS Assays

All samples were performed on bench-top standard equipment form Agilent Technologies consisting of model 6890N Gas chromatograph coupled to 5973 Mass Selective Detector operated in the PCI mode using ammonia as the reagent gas, and equipped with a model 7683 Series injector. Injections (1 μl) were performed at 300° C. in pulsed-splitless mode (injection pulse pressure 35 psi). The carrier gas was high-purity helium at a constant flow-rate of 0.7 ml/min. An Agilent Technologies-type HP-5 capillary column (50 m×0.2 mm inner diameter×0.5 μm phase thickness) was used under the following conditions: 170° C. for 1 min, increased by 10° C./min until 210° C., 5° C./min until 280° C. and then by 20° C./min until 325° C. At the end of each run, the temperature was kept at 325° C. for 8 min to clean the column. The GCMS transfer line was at 300° C., the ion source and quadrupole temperatures were at 300° C. and 176° C., respectively. The electron energy and emission current was at 65 eV and 242 mA respectively, and ammonia pressure (10 torr) was maintained at 1 ml/min. The following ion set was monitored with a dwell time of 50 ms per ion for the analysis of DHN, [$^2$H]DHN (reduced HNE), and the internal standard [$^2$H$_{11}$]DHN at m/z 257, 258 and 268, respectively. Alternatively one could also monitor the ion set 389, 390 and 400, which corresponds to the M+H+ion, using a lower ion source temperature [18], to confirm peak identity. However, in this example, a better MS signal was obtained using the former ion.

Quantities of DHN- and HNE-protein adducts that are reported in this study represent average of duplicate or triplicate sample injections. GC peak areas for the DHN and [$^2$H]DHN peaks, determined by computer integration, were corrected for light isotopic impurities of the internal standard [$^2$H$_{11}$]DHN and for naturally occurring heavy isotopes, respectively. Quantities of DHN and [$^2$H]DHN were calculated using corrected areas and from the quantity of internal standard added to each sample as previously described [8A].

Method Validation

The following method validation parameters were determined. (i) Accuracy was calculated from: [1-(GCMS measured quantity/standard quantity)]×100. (ii) Precision or the relative standard deviation (RSD) was calculated from: SD *100/mean. (iii) The limit of detection (LOD) represents the minimum quantity of standard DHN solution that can be processed and assessed with good accuracy and precision. (iv) The limit of quantification (LOQ) represents the minimum quantity of protein-derived DHN and HNE that can be assayed in blood or plasma samples with an appreciate precision. It was determined by analyzing increasing volume (50, 100, 250, 400 and 500 μl) of blood and plasma in duplicate samples. (v) The intra- and inter-assay RSD for the GCMS analysis were determined by injecting one sample eight times in one day and (ii) five samples on three different days, respectively. Intra- and inter-assay RSD for the whole analytical procedure were determined by processing (a) on the same day, nine samples obtained from a pooled blood sample collected from Wistar rats, and (b) on three different days, blood samples collected from five Wistar rats and frozen in separate aliquots. Inter-assay RSD values were also obtained for the analyses of four different blood samples from Wistar rats before and after 9 months of sample freezing at −80° C. Finally, to test the specificity of the signal corresponding to HNE, blood samples were pooled and divided 6 fractions, 3 fractions were treated with NaBH4 and 3 with NaB$^2$H$_4$.

Statistical Analysis

Data are expressed as mean±SD or SE. The two-way ANOVA was used to test for significant differences in the effect of (i) disease development and progression in SHR, (ii) age, and (iii) the interaction of disease and age, followed by a Bonferroni multiple-comparison post-test.

Results (Example 3)

Method Validation

Figure 2:
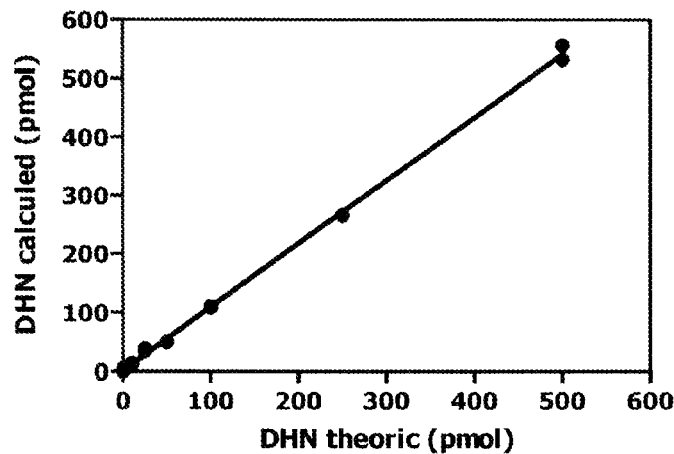
FIG. 2, in a X-Y graph, illustrates a standard curve obtained for DHN demonstrating the linearity of the GCMS assay; DHN standard solutions of 1 to 500 pmol were processed for analysis in duplicate; a regression line is shown including the 95% confidence intervals (slope: $1.079 \pm 0.009$; y-intercept: $2.2 \pm 1.6$; $p<0.0001$; $R2=0.999$)

The GCMS method depicted in FIG. 1 was evaluated for the following parameters: LOD, LOQ, precision, reproducibility, and robustness. The limit of detection (LOD) determined with DHN standard solutions, was estimated to be 50 pmol, based on the poor accuracy obtained when analyzing quantity below 50 pmol, between 16 and 76%, compared to values >90% for quantity between 50 and 500 pmol (Table 2). The calibration curve was linear in this range of DHN concentration tested (FIG. 2), with RSD values <4%.

TABLE 2

Calibration data obtained for a GCMS assay of DHN standard solutions used in a method for detecting a biomarker of oxidative stress in a biological sample in accordance with an embodiment of the present invention.

| Quantity added (pmol) | Quantity measured (pmol; mean ± SD) | Accuracy (%) | Precision (RSD %) |
|---|---|---|---|
| 1 | 6.3 ± 0.7 | 16 | 12 |
| 10 | 13.1 ± 0.8 | 76 | 6.3 |
| 25 | 37.1 ± 2.9 | 67 | 7.8 |
| 50 | 50.7 ± 0.3 | 99 | 0.6 |
| 100 | 110 ± 2 | 91 | 1.8 |
| 250 | 266 ± 0.4 | 94 | 0.2 |
| 500 | 545 ± 17 | 92 | 3.2 |

Standard solutions of 1 to 500 pmol DHN were processed for GCMS assay in duplicate.

Figure 3:
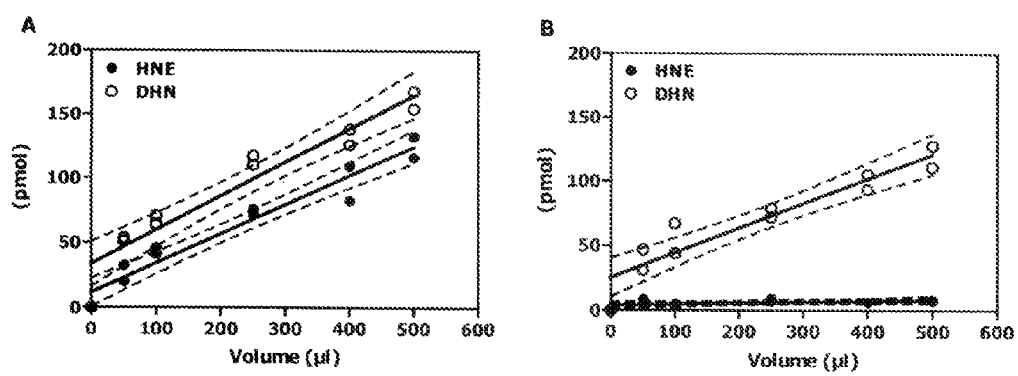
FIG. 3, in X-Y graphs, illustrates calibration curves obtained for the GCMS assays of protein-derived HNE and DHN in increasing volumes of (panel A) blood and (panel B) plasma, the assays having been performed in accordance with an embodiment of the present invention; samples for the various volumes were processed for analysis in duplicate; regression lines with 95% confidence intervals are shown: (panel A) HNE: slope=$0.23 \pm 0.02$, y-intercept: $12 \pm 5$, $R2=0.944$, $p<0.0001$; DHN: slope=$0.26 \pm 0.03$, y-intercept: $34 \pm 8$, $R2=0.922$, $p<0.0001$; and (panel B) HNE: slope=$0.008 \pm 0.004$, y-intercept: $4 \pm 1$, $R2=0.346$, NS; DHN: slope=$0.19 \pm 0.02$, y-intercept: $26 \pm 7$, $R2=0.891$, $p<0.0001$.

The GCMS method depicted in FIG. 1 was evaluated for the following parameters: LOD, LOQ, As for the method LOQ, there was a linear relationship for the analysis of protein-bound HNE and DHN in whole blood (FIG. 3, panel A), although the positive values for the y-intercepts, which fall in the LOD range, indicated a constant bias. Hence, the y-intercept values were taken as background and subtracted from all calculated experimentally determined values. A similar result was obtained for the analysis of protein-bound DHN in plasma (FIG. 3, panel B), but values for protein-bound HNE in plasma felt below the method LOD. A good precision (RSD <12%) was obtained for the measured values of protein-bound HNE and DHN in blood, and DHN in plasma. The LOQ of the method was estimated at 60 μmol, corresponding to about 250 μl samples. However, in routine applications, the practical method LOQ chosen was >80 µmol, corresponding to 400 µl samples, to ensure optimal precision.

Figure 4:
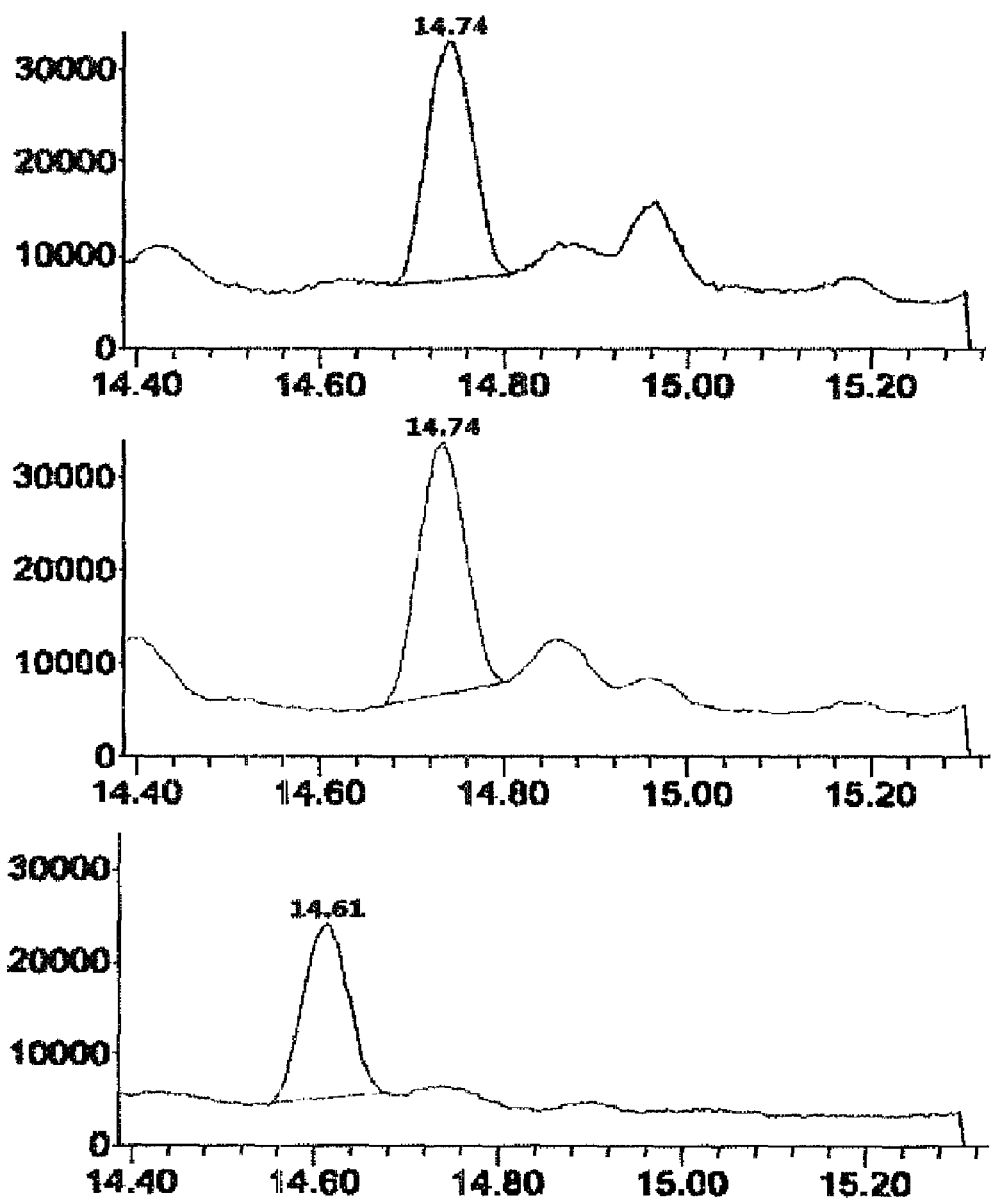
FIG. 4, in X-Y graphs, illustrates selected ion monitoring chromatograms of ion m/z 257 (upper chromatograms), m/z 258 (middle chromatograms) and m/z 268 (lower chromatograms) corresponding to DHN, HNE, and the deuterated internal standard [$^2H_{11}$]DHN, respectively, obtained from the processing of a representative blood sample from 30 week-old spontaneously hypertensive rats (SHRs), which was processed in accordance with an embodiment of the present invention.
Figure 5:
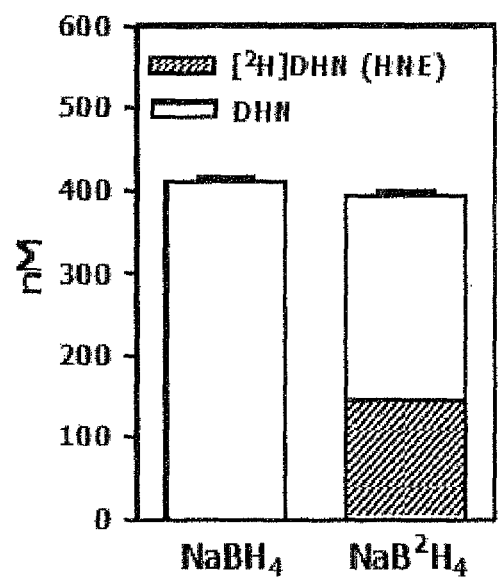
FIG. 5, in a bar chart, illustrates the specificity of the HNE signal obtained using a method in accordance with the present invention, the specificity being demonstrated by the treatment of parallel blood samples with $NaBH_4$ and $NaB^2H_4$, which converts HNE to DHN (ion m/z 257) and [$^2H$]DHN (ion m/z 258), respectively; there was no detection any quantity of protein-derived HNE signal following $NaBH_4$ treatment, while the measured quantity of protein-derived DHN corresponded to that of DHN plus HNE assessed following treatment with $NaB^2H_4$; Data are means±SE of triplicate determinations.

Table 3 summarizes the repeatability data for the assay of protein-bound HNE and DHN in 400 µl blood. FIG. 4 shows typical SIM chromatograms of a representative 400 µl blood sample collected from 30-week-old SHR. The intra- and inter-assay RSD were ≤11% for the GCMS analysis of whole blood samples and ranged between 10 and 20% for the whole method. Finally, the following additional data support also the robustness of our method. First, RSD values obtained for the analyses of protein-bound HNE and DHN in blood samples from Wistar rats after 9 months indicate the stability of these adducts upon sample freezing at −80° C. (Table 3). Second, the specificity of the HNE signal (ion 258) was demonstrated by treatment of parallel samples with $NaBH_4$ and $NaB^2H_4$, which converts HNE to DHN (ion m/z 257) and [$^2H$]DHN (ion m/z 258), respectively. While we did not detect any quantity of protein-derived HNE signal (ion 258) following $NaBH_4$ treatment, the measured quantity of protein-derived DHN (ion m/z 257) corresponded to that of DHN plus HNE assessed following treatment with $NaB^2H_4$ (FIG. 5).

As currently described, one technician can process about 80-100 samples per week. The variation between different assays (10-20%) is smaller than that between subjects (30-40%). Further, the precision observed in the LOQ determination compares well with GC/LC-MS assay of plasma isoprostanes [9A] or nitrotyrosine [10A], which are used as markers of oxidative and nitrosative stress, respectively. Moreover, while the stability of LPO-derived products in biological samples has often been considered a major problem [11A], we found that levels of HNE- and DHN-protein adducts were little affected by storage of samples for 9 months at −80° C. (Table 3). Although this may be attributed to the greater stability of these protein adducts compared to free HNE, Spies-Martin et al (2002) reported similar levels of free HNE in tissue samples before and storage for 22 months at −80° C. [12A]. Nevertheless, we consider relatively important to either freeze or process immediately all collected blood samples in EDTA as well as to rapidly treat samples with $NaB^2H_4$ to stabilize HNE.

In this study, the modified GCMS method was successfully applied to the analysis of circulating HNE- and DHN-protein adducts in rats. HNE-protein adducts were detected in blood,

TABLE 3

Summary of reproducibility data for the GCMS assay of HNE- and DHN-protein thioether adducts in 400 µl blood in accordance with an embodiment of the present invention.

| | GC-MS INJECTION | | GC-MS METHOD | | |
|---|---|---|---|---|---|
| Measured compound | Intra-assay (n = 8) RSD (%) | Inter-assay (n = 5) RSD ± SD (%) | Intra-assay (n = 9) RSD (%) | Inter-assay (n = 4) RSD ± SD (%) | 9 months of freezing (n = 4) RSD ± SD (%) |
| HNE | 3.4 | 7.9 ± 6.0 | 11 | 20 ± 9 | 26 ± 15 |
| DHN | 8.2 | 11 ± 6 | 11 | 10 ± 6 | 14 ± 6 |

The intra- and inter-assay RSD for the GCMS injection and processing of whole blood samples on different days were determined as described in Materials and Methods. Data are means±SD of 4-9 separate determinations, as indicated.

Circulating Levels of HNE- and DHN-Protein Adducts in SHR and Wistar Rats

Figure 6:
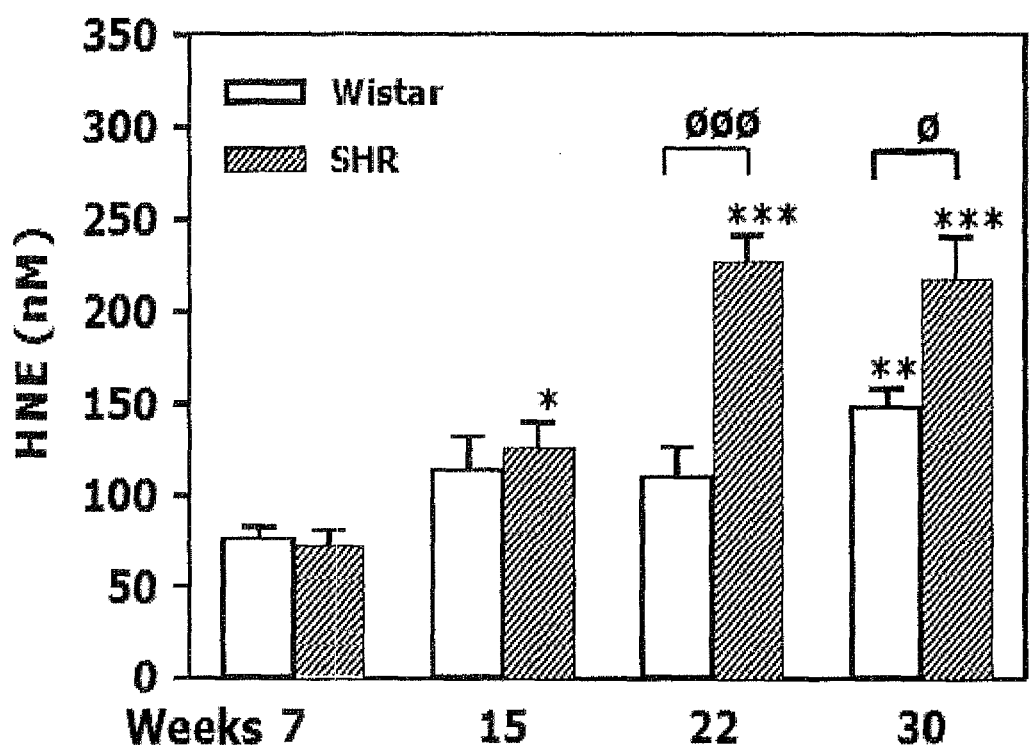
FIG. 6, in a bar chart, illustrates levels of HNE- protein thioether adducts in blood of SHR and Wistar rats at various ages obtained using a method in accordance with an embodiment of the present invention, samples (400 ml) of blood collected from 7-, 15-, 22- and 30-wk-old SHR and Wistar rats having been processed for GCMS analysis; Data are means±SE of 8-13 rats; statistics: Two-way ANOVA followed by the Bonferroni multiple-comparison post-test; effect of disease: SHR versus Wistar, øø$p<0.001$; ø$p<0.05$ Effect of age, vs. 7 weeks, *$p<0.05$, $p<0.01$, *$p<0.001$.

FIG. 6 present data on the levels of protein-bound HNE assessed in blood collected from SHR and Wistar rats at various ages. According to the two-way ANOVA, blood levels of HNE-protein adducts were significantly increased with disease progression and age. Compared to Wistar rats, SHR showed significantly greater blood levels of HNE-protein adducts starting at 22 weeks. The observed differences in the circulating levels of protein-bound HNE with age, or between SHR and Wistar rats, cannot be attributed to variations in blood protein levels, which were similar at all times (between 230 and 274 mg/ml). In contrast to protein-bound HNE, levels of protein-bound DHN in blood (FIG. 7) or in plasma (data not shown) did not vary with disease or age.

Discussion (Example 3)

In this study, a GCMS method for relatively precise quantitation of HNE- and DHN-bound to circulating thiol-containing proteins was validated. The method involves stabilisation of HNE through reduction to its deuterated alcohol [$^2H$]DHN, treatment of samples with Raney Nickel, and the use of a deuterated internal standard, [$^2H_{11}$]DHN. The proposed method was characterized for the following parameters: LOD, LOQ, precision, reproducibility, and robustness.

but not in plasma samples. This finding concurs with the observations of Kinter et al. [13A] who assessed HNE free or bound in Schiff base residues as an oxime derivative by GCMS. Further, Oliver et al. demonstrated the accumulation of oxidatively modified proteins in erythrocytes [14A]. Finally, HNE, which is predominantly detected in biomembranes rather in the aqueous phase [15A], reacts rapidly in vitro with the sulfhydryl group of cysteine residues from erythrocyte membrane proteins to form Michael-type adducts. Little is known about the half-life of blood HNE-modified proteins, but it is likely to be greater than free HNE. In fact, HNE-modified proteins may reflect the flux, rather than the circulating levels, of this LPO product [16A]. This cumulative record of oxidative injury may provide a sensitive measure of oxidative stress-related events involving bioactive HNE. By analogy, glycosylated hemoglobin reflects long term glycemic control [17A].

The concentration of protein-bound HNE that was measured in blood samples varied between 0.07-0.22 mM. These values fall in the range of concentrations reported for plasma free HNE (0.026-0.85 mM) [11A, 12A, 13A, 18A], but are lower than those for HNE-derived 2-pentylpyrroles (8-35 mM) [16A], while greater than those for isoprostanes (35-356 pg/ml) [19A-21A] or nitrotyrosine (2-5 nM) [10A,22A,23A]. Based on an average protein content of 250 mg/ml and assuming an average protein molecular mass of 30,000, a concentration of 0.07-0.25 mM of protein-bound HNE in blood implies that between 0.0008-0.003% of blood proteins is modified by HNE. This percentage is lower than the one that was calculated from the previously determined levels of HNE-protein adducts in ischemic hearts (approximately 0.025%)[1A]. However, it is compatible with the observed 1 to 8% protein modification observed in vitro when mammalian cells are incubated with 100 μM HNE [24A], if one takes into account that circulating free HNE concentration is <1 μM.

Figure 7:
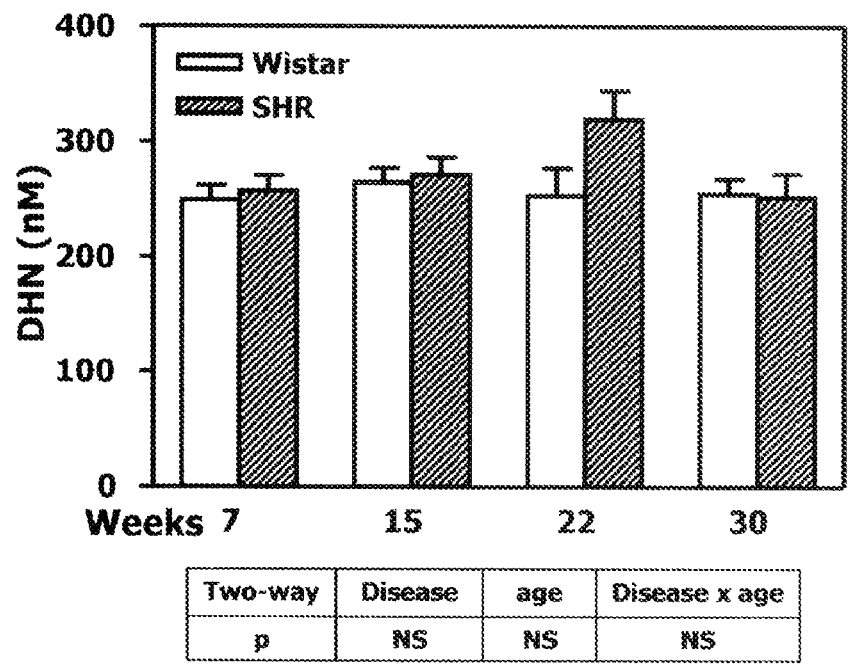
FIG. 7, in a bar chart, illustrates levels of DHN-protein thioether adducts in blood of SHR and Wistar rats at various ages, the levels having been obtained using a method in accordance with an embodiment of the present invention; data are means±SE; statistics: NS; Two-way ANOVA followed by the Bonferroni multiple-comparison post-test.

Results from this study demonstrate increased levels of HNE-protein adducts in blood of SHR with disease progression and aging, a finding that suggests that these protein adducts are circulating biomarker of oxidative stress-related events involving bioactive HNE in this animal model. The SHR develops hypertension and left ventricular hypertrophy between 9 and 14 weeks [25A,26A]. At 15 weeks, the hypertrophy is compensated, while at 30 weeks, SHR exhibit increased cardiomyocyte death by apoptosis, the latter being linked to transition from compensated to decompensated hypertrophy [48]. The increase in circulating HNE-protein adducts found in SHR concurs with the presence of enhanced oxidative stress, which was documented as early as 4 weeks of age [27A]. This raise has been attributed to increased superoxide anion production due to dysfunctional nitric oxide synthase activity [6A] and/or angiotensin II-stimulated NAD(P)H oxidase activity in the vascular wall [28A]. A persistently greater accumulation of myocardial HNE-protein adducts in SHR compared to control rats was also found, an effect that was affected by disease progression and age [7A]. The fact that the increase in HNE-protein adducts in blood occurred at a later age than in the vascular wall or in the heart (22 versus 7 weeks) may suggest that in SHR, HNE formation occurs predominantly at an intracellular site. A greater concentration of HNE-protein adducts in tissues compared to interstitial fluids was reported by others [29A], suggesting that accumulation of circulating HNE-protein adducts may reflect the global status of HNE production versus its detoxification in all body tissues and organs. In this regard, it was found that circulating levels of protein-bound DHN, which may originate from the enzymatic reduction of HNE-protein adducts by the aldose reductase [30A], were not affected by disease or age (FIG. 7). Hence, the increase in the proportion of HNE-to-DHN bound to circulating thiol proteins suggest an imbalance between HNE production versus detoxification with disease progression and aging, in the favor of the former process.

In summary, the GCMS method herein described and characterized quantifies HNE-protein thioether adducts in blood with relatively good precision and reproducibility. Using this method, it was showed that circulating HNE-protein adducts increase with disease progression and age in SHR, an animal model of cardiomyopathy that displays enhanced oxidative stress. Collectively, the results of this study suggest the potential usefulness of HNE-protein thioether adducts measured in whole blood as marker of oxidative stress-induced LPO events involving bioactive HNE in heart diseases and aging.

It is hypothesized that a kit for assessing the presence of a biomarker of oxidative stress in a sample could be used instead of the above-described method. Also, it is hypothesized that alternative method may be used to detect a biomarker of oxidative stress. In an example of such a method, the method includes contacting the sample with an antibody which binds to the stabilized biomarker of oxidative stress under conditions which allow binding of the stabilized biomarker of oxidative stress to the antibody and detecting the presence of bound antibody in the sample.

Example 4

A series of studies was conducted in spontaneously hypertensive rats (31A-33A), which provided the basis for exploring in vivo the potential link between HNE and cardiac function. The SHR is a well-established model of genetic hypertensive cardiomyopathy associated with insulin resistance (34A). It develops hypertension and left ventricular hypertrophy between 9 and 12 weeks (35A). At 15 weeks, the hypertrophy is compensated and functional symptoms of decompensation appear after 18-24 months of age. The SHR displays enhanced oxidative stress in the vascular wall (36A), which responds to antioxidant treatment (37A). Further to the finding of an accumulation of myocardial HNE-protein adducts in SHR starting at 7 weeks (33A), a GCMS method was validated to quantify HNE-protein thioether adducts in blood (HNE-P) and found relatively high circulating HNE-P in SHR starting at 22 weeks of age (31A). Hence, in this example, circulating HNE-P was correlated with cardiac function in vivo and tests were performed to evaluate the impact of an antioxidant treatment with Probucol (38A).

Method (Example 4)

Animals

Experiments were approved by the local animal care committee in compliance with guidelines of the Canadian Council on Animal Care. After one week of acclimatization, 18-wk-old male SHR (Charles River, St. Constant, Canada) were randomly assigned to receive daily an intraperitoneal injection of 10 mg·kg-1 body weight Probucol (P) dissolved in corn oil or the vehicle (V). Body weight was assessed daily. At 22 weeks of age, rats were sacrificed. Blood was collected under ketamine/xylazine anaesthesia (87.5 mg/12.5 mg·kg-1, i.m.) by jugular vein puncture with a 5-ml syringe precoated with EDTA (10.8 mg) and butylated hydroxytoluene (0.0496 mg), and immediately frozen in liquid nitrogen.

Blood Pressure and Cardiac Function.

Non-invasive systolic arterial pressure was measured and transthoracic echocardiographic evaluation was performed at baseline and at the end of treatment, using the tail-cuff method and S12 phased-array transducer with a standard echocardiographic system (Sonos 5500, Hewlett-Packard, Andover, Mass.) under isoflurane anesthesia, respectively. We herein report echocardiographic parameters reflecting diastolic function only, since systolic function was reported to be unchanged in SHR at 18-22 weeks (29A). In the apical 4-chamber view, transmitral E wave deceleration time (EDT) and deceleration rate (EDR) were measured using pulsed-wave Doppler, and mitral propagation velocity (Vp) was studied through color M-mode spectrum. LV isovolumic relaxation time (IVRT) was measured in the 5-chamber view using continuous-wave Doppler and corrected (IVRTc) with the R-R interval taken from simultaneously recorded ECG. M-mode at the aortic valve level in the parasternal long axis view was used to measure left atrial (LA) dimensions in both cardiac diastole (LADd) and systole (LADs), from which we calculated LA fractional shortening (LAFS). The average of three consecutive cardiac cycles was used for each measurement. Circulating HNE-P. HNE-P was quantified in 400 μl whole blood collected at the end of treatment, by GCMS as described in Example 1.

Data Presentation and Statistical Analysis.

Data are means±SEM. Values for the various parameters measured (body weight, systolic blood pressure and cardiac functions) are reported as percentages of pre-treatment values. Statistical significance of differences between and within groups (before vs after treatment) was assessed using unpaired and paired t-tests, respectively. Correlation coefficients were calculated by linear regression analysis. A value of p≦0.05 was considered significant.

Results (Example 4)

Hemodynamics and Cardiac Function.

Figure 9:
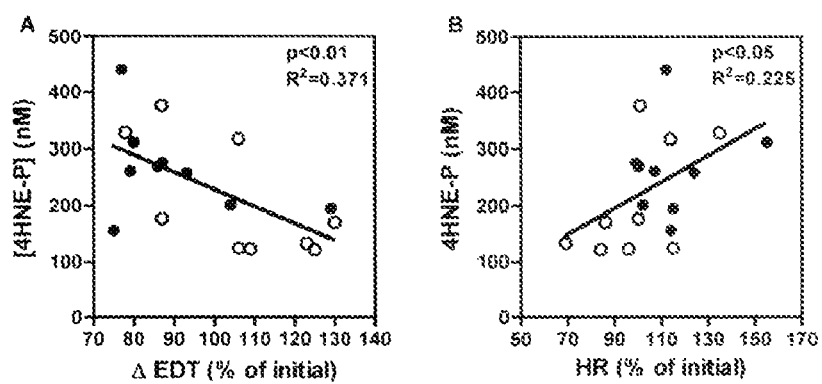
FIG. 9, in X-Y graphs, illustrates correlations between circulating HNE-P and both deterioration of diastolic function (as reflected by EDT) (A) and increased heart rate (B) in SHR after receiving Probucol (·) or vehicle (o) during 4 weeks.

During the 4-week treatment, SHR from both groups depicted a similar 7-8% increase in body weight and systolic blood pressure (V: 7.6±0.2, P: 7.9±0.7; and V: 8.2±2.4, P: 8.3±2.0%, respectively; p<0.05). However, SHR receiving vehicle depicted a worsening of indexes of diastolic function. Changes in (i) EDT (decreased; FIG. 9, panel A) and EDR (increased; 18±6%; p≦0.05) reflect a loss of LV compliance or increased stiffness, while those in (ii) Vp (decreased; FIG. 9, panel B) and IVRTc (increased: 8.9±7.0%; p≦0.05) indicate impaired LV relaxation. Heart rate was also increased by 20% (FIG. 9, panel C). All these detrimental functional changes were not observed in the Probucol group. In this group, LV diastolic function was preserved, resulting in diminished LA structural and functional remodeling; this is reflected by changes in LADd (decreased: −17.9±6.4%; p≦0.05) and LAFS (increased; 16.1±5.4%; p≦0.05).

Circulating HNE-P.

Figure 8:
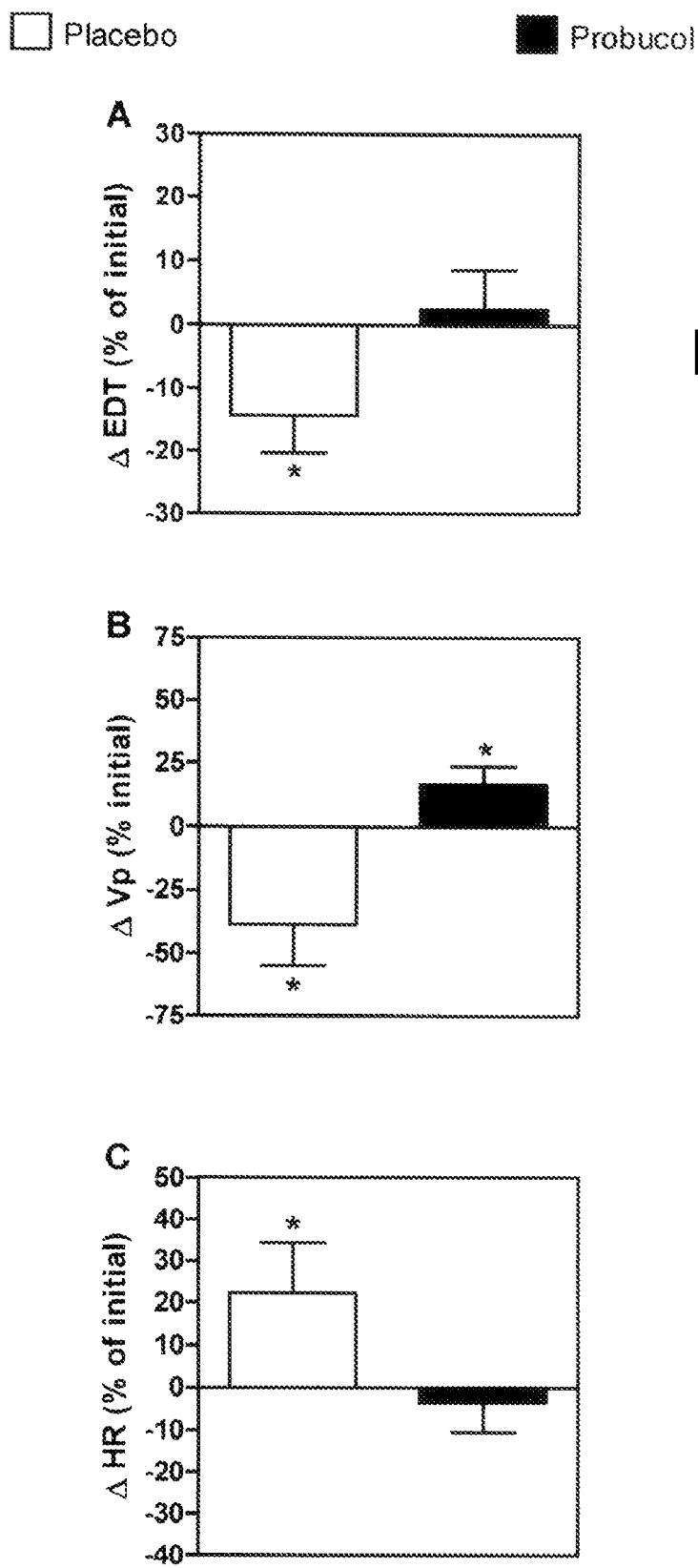
FIG. 8, in bar charts, illustrates changes in diastolic function (panels A &B) and heart rate (panel C) in SHR after receiving Probucol or vehicle during 4 weeks; diastolic dysfunction is reflected by a decrease in indexes of LV compliance (EDT: E wave deceleration time) and relaxation (Vp: mitral flow propagation velocity; results are depicted as percent of pre-treatment values; effect of treatment: *$p<0.05$.

Circulating HNE-P, which was assessed at the end of treatment in 22-wk-old SHR correlated with indexes of diastolic dysfunction (EDR: $R^2=0.518$, p<0.001; EDT: $R^2=0.371$, p<0.01 (FIG. 8, panel A)) and with heart rate (FIG. 8B). Probucol treatment lowered median [min-max] (P: 170.5 [122.5-376.0]; V: 261.3 [157.0-441.5]) and mean (P: 208.2±34.1; V: 263.8±27.4) values of circulating HNE-P by 35% and 21%, respectively (p=0.1).

Discussion (Example 4)

In this example, the link between circulating HNE-P levels and cardiac function, was examined in SHR and the impact of Probucol treatment was tested. 18-22-wk-old SHR were used based on finding of high circulating HNE-P in these rats at this age (31A and Example 1). At 18-22 wks of age, the SHR is hypertensive and depicts a compensated cardiac hypertrophy (39A). The finding of a worsening of diastolic function in 18-wk-old SHR receiving vehicle for 4 weeks concurs with data from Slama et al. (2004) (40A). In this study, treatment of SHR with Probucol attenuated the deterioration of diastolic function and improved left atrial function, an effect that was independent of blood pressure.

Circulating HNE-P levels, which were assessed at the end of treatment, correlated positively with deterioration of diastolic function in SHR, specifically reduction of LV compliance. Furthermore, a positive correlation between circulating HNE-P and increased heart rate was observed. Increased heart rate is factor that has been linked with morbidity and mortality in patients with coronary artery disease (41A). Recently, a correlation was reported between immunohistochemically determined HNE-protein adducts in the right ventricle of patients with hypertrophic cardiomyopathy and indexes of cardiac dysfunction (42A). Probucol decreased circulating HNE-P levels, but only a relatively small statistical significance was observed for this result. It is hypothesized that this resulted from a type II error given the small number of animals in each group.

The correlation data presented hereinabove suggest a potential role of HNE in the pathogenesis of diastolic dysfunction and in the regulation of heart rate in SHR. A hypothetical mechanism that may explain this results is presented hereinbelow. Isolated hearts exposed to HNE depict vasodilation, reduction of systolic function and contractile failure (43A). In isolated rat ventricular myocytes, HNE exerts proarrhythmic effects possibly due to modification of cysteine residues from ion channel proteins (44A). It can also depress contraction, possibly through mitogen-activated protein kinase activation (45A). Among many potential pathogenic mechanisms, one that appears to have specific relevance to this study is fibrosis. This process appears to be a determinant of LV stiffness, including in SHR (46A-48A), which could be activated by HNE through TGFb1 signaling (50A), but reduced by Probucol (49A).

In summary, the results of this example show that left ventricular diastolic function worsens in control SHR from 18 to 22 weeks, leading to a restrictive pattern of diastolic dysfunction, which can be improved by Probucol treatment. The observed correlations between HNE-P and both diastolic dysfunction and heart rate provide additional evidence supporting a role for this aldehyde in the pathophysiological events linked to disease progression in SHR. Ultimately, circulating HNE-P may be correlated with specific pathogenic events that could then become a target for antioxidant therapy.

Example 5

The blood levels of HNE-protein adduct was assessed as described hereinabove in 71 human subjects suffering from chronic heart failure. The HNE-protein concentrations averaged 214±67 nM. The levels were correlated to the New York Heart Association Class ($R^2=0.33$; p<0.05), suggesting its association with disease severity.

Further to the above-described examples, adduction of HNE to different amino acids in protein was investigated.

Example 6

Materials and Methods (Example 6)

Chemicals

Raney nickel was obtained from Laboratoire Mat (Montreal, Quebec, Canada). Poly-L-lysine, poly-L-histidine, poly-L-arginine, poly-L-serine, poly-L-glutamate, butylhydroxytoluene, 2,4-dinitrophenylhydrazine (DNPH) were purchased from Sigma Chemical Co (St Louis, Mo.), and bovine serum albumin from Serologicals Protein Inc. (Kankakke, Ill.). Poly-L-cysteine:Lglutamic acid (20:80) was synthesized by Genscript Corp (San Francisco, Calif.). Organic solvents and acids were from Fischer Scientific (Nepean, Ontario, Canada). Unlabeled and [2H3]labeled HNE were from Cayman (Ann Arbor, Mich.). Sodium borodeuteride (NaB2H4), $^2H_2O$, and trans-4-hydroxy-2-nonenal-[5,5,6,6,7,7,8,8,9,9,9-$^2H_{11}$]([$^2H_{11}$]HNE)diethyl acetal were supplied by Cambridge isotope Laboratories (Andover, Mass.) and CDN Isotopes (Montreal, Quebec, Canada). The stock solution of the internal standard [$^2H_{11}$]1,4-dihydroxy-2-nonene was prepared as previously described [22]. All aqueous solutions were prepared with water purified milli-Q-system (Millipore, Montreal, Quebec, Canada).

Preparation of HNE-Modified PAA

Poly-L-lysine (Mr=150,000-300,000), poly-L-histidine (Mr>5,000), poly-L-arginine (Mr>70,000), poly-L-cysteine-L-glutamate (Glu/Cys:5/1, units), poly-L-arginine, poly-Lserine, poly-L-glutamate (Mr=50,000-100,000) (2 mg/ml) dissolved in 50 mM sodium phosphate buffer, pH 7.4, were incubated with HNE or [9,9,9-2H3]HNE (2 mM) at 37° C. for 15 h. Then, the reaction mixture was dialysed for 24 h against 50 mM sodium phosphate buffer pH 7.4 (3 buffer changes, 1/200 v/v) to remove unreacted HNE.

Incubation of Bovine Serum Albumin with HNE

Bovine serum albumin (50 or 600 µM) was incubated with HNE (10 µM to 2 mM) in 50 mM sodium phosphate buffer, pH 7.4 at 37° C. for up to 15 h. The reaction mixture was dialysed as described for PAA incubation mixtures.

Figure 10:
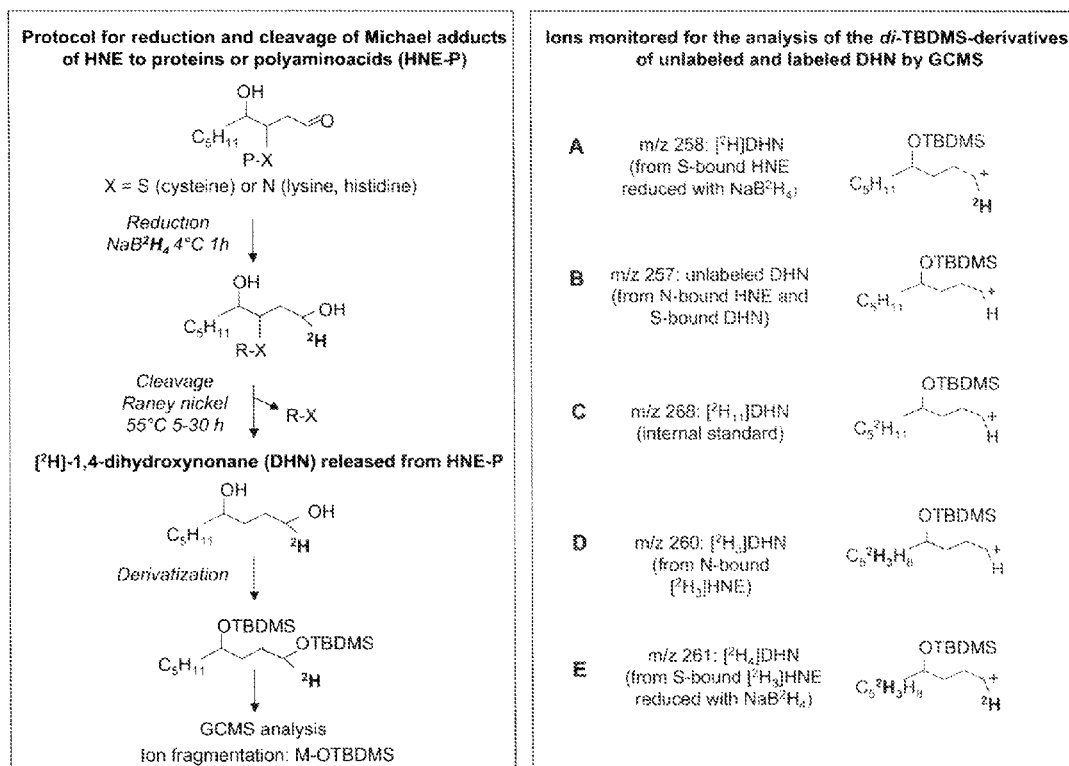
FIG. 10, in a schematic view, illustrates an overview of the experimental protocol to quantify Michael adducts of HNE to proteins or polyamino acids (HNE-P) by gas chromatography-mass spectrometry (GCMS). The procedure involves reduction of bound HNE to [²H]DHN with NaB²H₄ followed by treatment with Raney nickel to release [²H]DHN, which is then converted to a di-t-butyldimethyl (TBDMS) derivative. Under our GCMS operating conditions, the latter derivative undergoes a loss of [O-TBDMS], resulting in the formation of an ion at m/z 258 (structure A). The figure depicts also the structure of the TBDMS derivative of other DHN species that are analysed in this study along with the origin of each signal for the analysis of blood or plasma samples: (i) unlabeled DHN: from nitrogen-bound HNE and cysteine-bound DHN (structure B; ion at m/z 257), (ii) [2H11]DHN: from the internal standard (structure C; ion at m/z 268), (iii) [2H3]DHN: from nitrogenbound [2H3]HNE (structure D; ion at m/z 260); and (iv) [2H4]DHN: from cysteinebound [2H3]HNE reduced with NaB2H4 (structure E; ion at m/z 261).an overview of an experimental procedure to quantify HNE and its metabolite DHN bound to a protein via thioether linkage in blood by isotope dilution GCMS in accordance with an embodiment of the present invention, the symbol * indicating the measured molecules.

Sample Treatment with NaB2H4 and Raney Nickel (FIG. 10)

Dialyzed solutions of HNE-modified PAA (2 mg/ml) or of albumin, and plasma and blood samples were either diluted (1/1000 for poly-L-cysteine-L-glutamate; 1/40 for other PAA and for albumin) or treated directly with 1 M NaB[$^2$H$_4$] at 4° C. for 1 h to reduce the free carbonyl group of HNE bound to PAA to a deuterated alcohol group. These reducing conditions were previously used for blood or tissue samples [22, 23], since they minimize artefactual production of HNE from lipid peroxidation during sample processing. Samples were treated with five volumes of cold ethanol (PAA) or with saturated sulfosalicylic acid (SSA) (albumin, plasma and blood samples), and centrifuged at 6500 rpm for 45 min at 4° C. The PAA, albumin or blood and plasma protein pellets were resuspended into 2 ml of guanidine (pH 7.2), spiked with 0.1-0.3 nmol of deuterated internal standard [$^2$H$_{11}$]1,4-dihydroxy-2-nonene and incubated with 1.7 g of Raney nickel catalyst for 5 to 30 h at 55° C. Control incubations were also conducted in the absence of Raney nickel catalyst. In selected experiments, we tested the impact of replacing water with $^2$H$_2$O, which was used either for dissolving the PAA or protein pellet and/or the Raney nickel. Following incubations, the sample supernatants were brought to pH<2 and extracted two times with ethyl acetate. The combined extracts were evaporated to dryness under N2 and reacted with N-methyl-N-(tert-butyldimethylsilyl)-trifluoroacetamide at 80° C. for 6 h.

DNPH Treatment of Blood and Plasma Samples

Aliquots of blood (0.4 ml) and plasma (0.5 ml) were treated with five volumes of 0.15% (w/v) of DNPH in 2 N HCl and incubated for 1 h at room temperature [27]. These mixtures were treated with 0.4 ml of SSA and after centrifugation, the precipitate was dissolved with 0.5 ml of 8 M guanidine hydrochloride. The samples were then treated with Raney nickel and derivatizated for GCMS analysis.

GCMS Analysis

The procedure for GCMS analysis has been previously described in details [22]. Briefly, a 1 µl aliquot was injected into a Agilent 6890 N GC equipped with an HP-5 capillary column (50 m×0.2 mm inner diameter×0.5 µm phase thickness) coupled to a 5973 detector operated in the positive chemical ionization mode with ammonia as the reagent gas at pressure of $10^{-3}$ Torr and an electron energy of 153 ev. The MS source and quadripole temperatures were set at 300° C. and 176° C. respectively. The GC column temperature was set at 170° C. for 1 min, increased by 20° C./min until 325° C. and kept at this temperature for 8 min. The following ions were monitored with a dwell time of 100 ms per ion for the analysis of the TBDMS derivatives of unlabeled or labeled DHN molecular species (see FIG. 10): (i) m/z=258 for [$^2$H]DHN (from bound HNE reduced with NaB$^2$H$_4$), (ii) m/z=268 for the deuterated internal standard [$^2$H$_{11}$]DHN. We also routinely monitored the ion at m/z 257, which corresponds to unlabeled DHN. For incubations with [$^2$H$_3$]labeled HNE, we monitored the ions at m/z 260 corresponding to [$^2$H$_3$]DHN, and at m/z 261 corresponding to [$^2$H$_4$]DHN (from bound [$^2$H$_3$]HNE reduced with NaB$^2$H4). All these ions results from the loss of [M-OTBDMS] from the molecular ions [M.]+. Concentrations of HNE-P that are reported in this study represent average of duplicate or triplicate sample injections. GC peak areas determined by computer integration, were corrected for naturally occurring heavy isotopes and light isotopic impurities of the internal standard [$^2$H$_{11}$]DHN. Concentrations were calculated using corrected areas and from the quantity of internal standard added to each sample as previously described [22].

Protein Carbonyl Assay

An aliquot (1 ml) of HNE-PAA solution was incubated for 1 h with 0.1% (wt/vol) DNPH in 2 M HCl at room temperature. After precipitation with 10 ml of cold ethanol to remove unreacted HNE, the HNE-PAA pellet was dissolved in 2 ml of 8 M guanidine hydrochloride, 13 mM EDTA, and 133 mM Tris (pH 7.4). UV absorbance was assessed at 365 nm. Concentrations are expressed as molar ratio [DNPH]/[AA] (mol/mol) and were calculated using a molar absorptivity coefficient of 21.0 mM/cm-1 [27].

Statistics

Data are presented as means±SEM (r13) or SD (n=2) and are representative of 2-7 experiments conducted in duplicates or triplicates.

Results (Example 6)

Experiments with PAA

FIG. 10 (left panel) illustrates the experimental procedure that was used based on our previous publication [22] to quantify sulfur and nitrogen-bound HNE via Michael adducts in the various experiments described below. Throughout the remainder of this document, we will refer to the chemical structure of the TBDMS derivatives of the various deuterated and non-deuterated DHN molecular species released by treatment with Raney nickel and analyzed by GCMS by selected ion monitoring of the indicated m/z values. For reference, FIG. 10 (right panel) lists the various ions that have been analyzed and their proposed origin for the analysis of a blood or plasma sample. It is noteworthy that the origin of a given GCMS signal may vary under other conditions; it will therefore be specified for each experiment.

Figure 11:
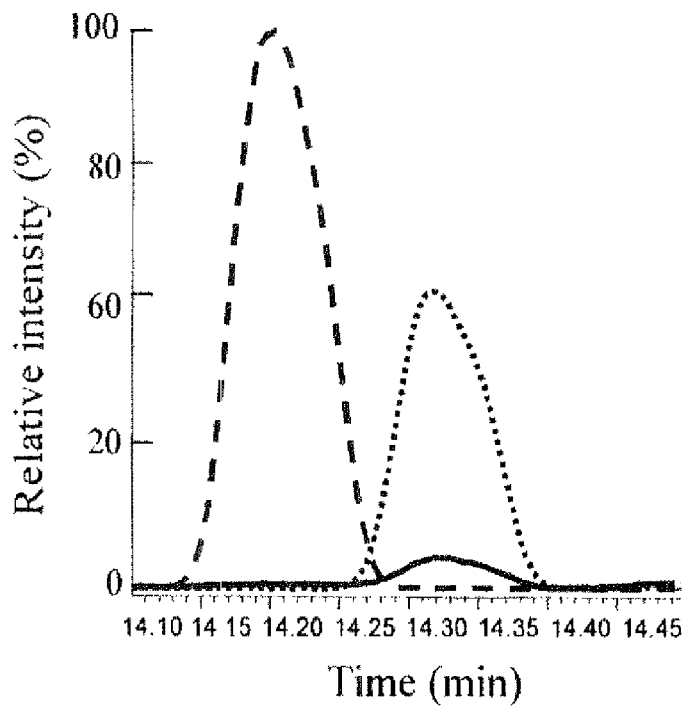
FIG. 11, in a X-Y graph, illustrates representative selected ion chromatograms of samples obtained from incubations of poly-L-cysteine-L-glutamate with HNE. Poly-L-cysteine-Lglutamate (cysteine:glutamate molar ratio 1:5, 30 units; 2 mg/ml corresponding to 3.3 mM of cysteine) was dissolved in 50 mM sodium phosphate buffer, pH 7.4 and incubated with HNE (2 mM) at 37° C. for 15 h. Following dialysis for 24 h to remove unreacted HNE, samples were processed as described in Methods and illustrated in FIG. 10. Data are shown as percent relative intensity uncorrected for the natural abundance in heavy isotopes. The origin of the signal at the various ions is indicated in parentheses.
Figure 12:
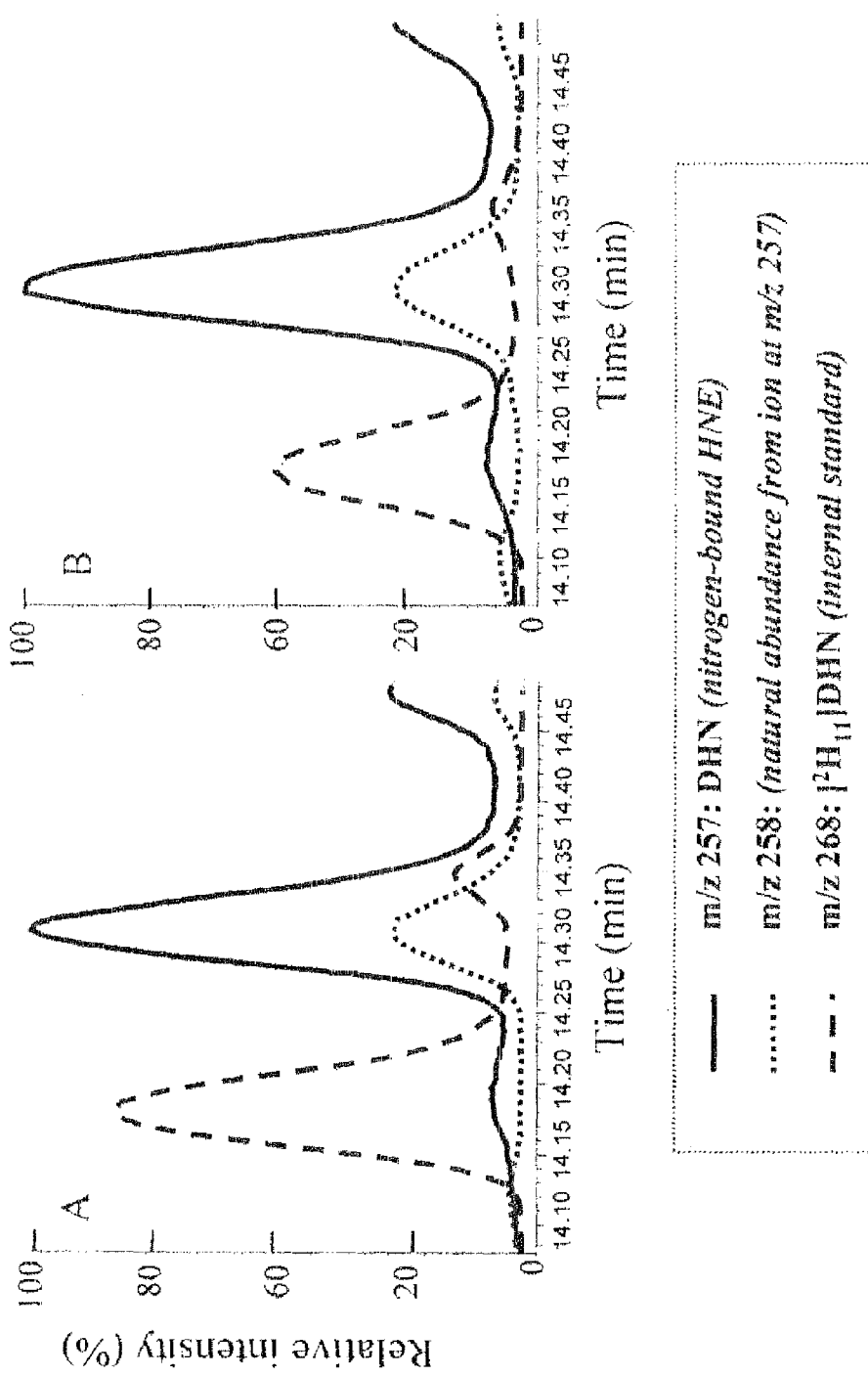
FIG. 12, in X-Y graphs, illustrates Representative selected ion chromatograms of samples from incubations of poly-L-lysine (A) or poly-L-histidine (B) with HNE. The indicated PAA histidine (2 mg/ml corresponding to 13.7 mM of lysine and 12.9 mM of histidine respectively) was dissolved in 50 mM sodium phosphate buffer, pH 7.4 and incubated with HNE (2 mM) at 37° C. for 15 h. Following dialysis for 24 h to remove unreacted HNE, samples were processed as described in Methods and illustrated in FIG. 10. Data are shown as percent relative intensity uncorrected for the natural abundance in heavy isotopes. The origin of the signal at the various ions is indicated in parentheses.

FIGS. 11 and 12 depict representative GCMS data for the analyses conducted with the various PAA, while Table 1 reports quantitative values obtained for these analyses by GCMS and by the protein carbonyl assay. It is noteworthy that for all these experiments, the dialyzed solution of HNE-modified PAA was diluted (¹⁄₁₀₀₀ for poly-L-cysteine-Lglutamate and ¹⁄₄₀ for other PAA) to obtain MS data of high accuracy (>90%) and precision (>2%). Specifically, we have previously shown that this is obtained for concentrations of DHN between 100-500 picomoles [22].

TABLE 1

Concentrations of HNE bound to the various polyaminoacids containing cysteine, histidine, lysine and arginine residues by gas chromatography-mass spectrometry by the carbonyl assay using spectrophotometry.

| PAA | GCMS assay (mol [DHN + [2H]DHN]/ mol AA) | GCMS assay (relative to CYS) | Protein carbonyl assay (mol DNPH/ mol AA) | Protein carbonyl assay (relative to CYS) |
|---|---|---|---|---|
| Cysteine | $5.7 \times 10^{-1}$ | 1 | $8.6 \times 10^{-2}$ | 1 |
| Histidine | $1.6 \times 10^{-3}$ | $2.8 \times 10^{-3}$ | $2.6 \times 10^{-3}$ | $3.0 \times 10^{-2}$ |
| Lysine | $1.2 \times 10^{-3}$ | $2.2 \times 10^{-3}$ | $9.4 \times 10^{-4}$ | $1.1 \times 10^{-2}$ |
| Arginine | $3.8 \times 10^{-5}$ | $6.8 \times 10^{-5}$ | n.d. | n.d. |

Data are expressed as molar ratio: [(DHN +[2H]DHN)]/[AA] and [DNPH]/[AA], respectively. Values are mean of 3-4 replicates determinations (CV<10) and representative of 2-3 experiments. ND: not determined. Incubation conditions and analyses are detailed in Material and Methods section. CYS:

cysteine; DHN: 1,4-dihydroxynonane; GCMS: gas chromatography-mass spectrometry; DNPH: diphenylhydrazine; PAA: polyaminoacids. n.d.: not detected.

GCMS Assay of HNE Adducts with Poly-L-Cysteine-L-glutamate.

FIG. 11 depicts representative selected ion chromatogram obtained following GCMS analysis of samples obtained from incubations of poly-L-cysteine-L-glutamate (2 mg/ml corresponding to 3.3 mM of cysteine) with 2 mM HNE (resulting in a ratio cysteine-to-HNE of 1.65). As expected, we observed a signal at m/z 258, which corresponds to [$^2$H]DHN (from HNE adducts reduced with NaB$^2$H$_4$; FIG. 10 structure A) released from the poly-L-cysteine-L-glutamate solutions incubated with HNE following treatment with Raney nickel for 15 h. There was little if any signal at m/z 257, which corresponds to unlabeled DHN (FIG. 10, structure B); the low signal may arise from light isotopic impurities in NaB$^2$H$_4$ and/or in the internal standard [$^2$H$_{11}$]DHN [28]. The larger signal at m/z 268 corresponds to the internal standard of [$^2$H$_{11}$]DHN. In additional experiments, in which we examined the impact of incubation time with Raney nickel at 55° C., we found that the quantity of DHN released from the poly-L-cysteine-Lglutamate was maximal after 5 h, and was constant for longer incubation period up to 30 h (data not shown). Furthermore, we have confirmed that incubation of poly-L-glutamate with HNE did not yield any detectable GCMS signal at m/z 258 nor 257.

GCMS Assay of HNE Adducts with Poly-L-Lysine and Poly-L-Histidine.

FIG. 12 shows representative GCMS analysis of samples from incubations of poly-L-lysine (FIG. 12, panel A) or poly-L-histidine (FIG. 12, panel B) (2 mg/ml corresponding to 13.7 mM of lysine and 12.9 mM of histidine respectively) with 2 mM HNE (resulting in ratios amino acid-to-HNE of 6.85 and 6.45, respectively). Unexpectedly, in both cases, we observed a predominant GCMS signal at m/z 257 corresponding to unlabeled DHN (FIG. 10; structure B). This contrasts with our finding of a predominant signal at m/z 258 corresponding to [2H]DHN (FIG. 10; structure A) for samples analyzed following incubations of HNE with poly-L-cysteine-L-glutamate (FIG. 11). Furthermore, in FIG. 12, the GCMS signal at m/z 258 has not been corrected for natural abundance of heavy isotopes (such as carbon 13 and deuterium) in unlabeled DHN. While this correction is essentially negligible for the ions at m/z 257 and 268, this explains most of the GCMS signal at m/z 258. Indeed, the contribution of the natural abundance signal at the m/z 258 ion is 21% of the magnitude of the base peak at m/z 257. After correction for the natural abundance, the GCMS signal left at m/z 258 becomes very low, representing only 11 and 5±2% of the total MS signal for poly-L-lysine or poly-L-histidine, respectively.

Hence, the analysis of solutions of poly-L-lysine and poly-L-histidine incubated with HNE resulted in a predominant GCMS signal at m/z 257, which is one mass unit less than that expected for HNE adducts reduced with NaB$^2$H$_4$ (m/z 258) and cleaved with Raney nickel. This result contrasts with that obtained for poly-L-cysteine-L-glutamate (FIG. 11). Also contrasting with the latter PAA was our finding that the GCMS signal at m/z 257 that was observed for solutions of poly-L-lysine and poly-L-histidine incubated with HNE required minimally 15 h of treatment with Raney nickel at 55° C. to reach a maximal value (data not shown). It is noteworthy that the GCMS signal was undetectable when the Raney nickel step was omitted from the sample preparation procedure (data not shown). PAA-bound HNE determined by GCMS vs the protein carbonyl assay. In order to provide additional support for the release of HNE from the various PAA and more specifically for poly-L-lysine or poly-L-histidine following Raney nickel treatment, we have compared our GCMS assay to the protein carbonyl assay for the various PAA incubated with HNE.

As shown in Table 1, the quantity of HNE released from the various HNE-PAA solutions (expressed as: molar HNE-to-AA ratio) evaluated by GCMS were: cysteine (0.6)>>histidine (1.6×10$^{-3}$)>lysine (1.2×10$^{-4}$), concurring with the standard protein carbonyl assay. The levels of HNE were found to be very low for poly-L-arginine, but undetectable for poly-L-glutamate nor poly-L-serine. Hence, the order of reactivity of the various amino acids with HNE that we observed is consistent with literature results: cysteine>>histidine>lysine>>arginine [5]. It is noteworthy that for all analyses reported in Table 1, the % CV for the measured concentration was <10%.

Characterizing the GCMS Signal Obtained from HNE Adducts with Poly-L-Lysine and Poly-L-Histidine While the aforementioned data provided evidence that Raney nickel treatment can cleave adducts of HNE to PAA via carbon-nitrogen (C—N) bonds at 55° C. in addition to thioether links (C—S), additional experiments were conducted to better understand why GCMS signal is one mass unit less than expected for the analysis of solutions of poly-L-lysine and poly-Lhistidine incubated with HNE.

Incubation with [$^2$H$_3$]HNE. First, in order to provide additional evidence that HNE is at the origin of this GCMS signal, we incubated poly-L-lysine or poly-L-histidine with [$^2$H$_3$]HNE and processed the samples with NaB$^2$H$_4$ and Raney nickel as previously described for FIGS. 11 and 12. As can be seen from FIG. 13, which depicts results from representative samples from these experiments, the pattern of GCMS signals is similar to that of FIG. 12, except for the shift of three mass units. Specifically, the predominant GCMS signal is now observed at m/z 260 (corresponding to [$^2$H$_3$]DHN; FIG. 10; structure D) instead of 257, thus demonstrating that it arises from [$^2$H$_3$]HNE. It is noteworthy that the signal at m/z 261 (which would be expected if bound [$^2$H$_3$]HNE had been reduced with NaB2H4; FIG. 10; structure E) becomes marginal after correction for natural abundance in heavy isotopes of the base peak at m/z 260, representing <10% of the total GCMS signal detected at both ions.

Incubation with $^2$H$_2$O.

Finally, we tested the possibility of a loss of deuterium through hydrogen exchange with the medium at the Raney nickel step. This was achieved by replacing H$_2$O by $^2$H$_2$O during Raney nickel treatment of solutions of poly-L-cysteine-L-glutamate or poly-L-lysine, which had been incubated with HNE and reduced with NaB$^2$H$_4$. For poly-Lcysteine-L-glutamate, we obtained data identical to that depicted in FIG. 11 (data not shown). However, with poly-L-lysine, we observed a shift in the MS signal from m/z 257 to m/z 258 (FIG. 14) corresponding to [$^2$H]DHN, the percentage of which was increased from 11±3% to 51±5% of the total MS signal (mean±SD, n=2). Similar results were obtained with solutions of poly-L-histidine incubated with HNE (data not shown). Note that addition of 2H2O at the NaB2H4 step with Raney nickel dissolved in unlabeled water did not result in such a mass shift.

Figure 15:
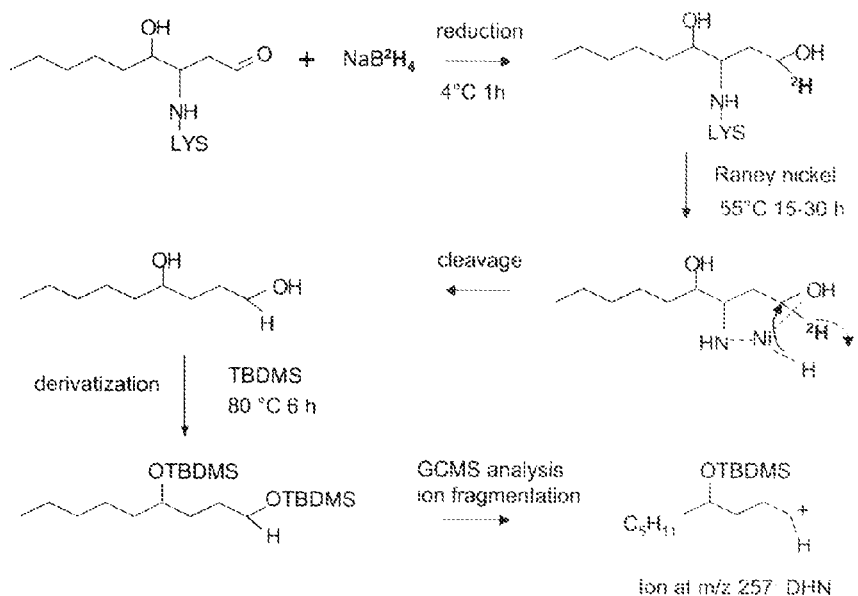
FIG. 15, in a schematic view, illustrates a proposed mechanism for deuteration of nitrogen-bound HNE during cleavage with Raney nickel. Although nitrogen-bound HNE may be converted to [²H]DHN by NaB²H₄, the incorporated deuterium may exchange with hydrogen of the Raney nickel catalyst or the medium. This may occur while reduced HNE is tied to the metal surface through the nitrogen atom. The proposed mechanism is illustrated with HNE bound to lysine through Michael addition, but would also occur for histidine. A longer residence time on the catalyst would explain our finding of a deuteration for lysine or histidine, but not for cysteine.

Hence, in summary, the results obtained concur with HNE being at the origin of the signal observed at m/z 257 for samples from experiments conducted with PAA-containing lysine and histidine. They also suggest that the loss of deuterium through hydrogen exchange with the medium at the Raney nickel step may explain why the GCMS signal that is observed at one mass unit less (i.e. at m/z 257 corresponding to DHN, FIG. 10 structure B) than that expected (i.e. at m/z 258 corresponding to [²H]DHN, FIG. 10, structure A). FIG. 15 illustrates the proposed scheme of reactions involved in the hydrogen exchange.

Experiments with Biologically Relevant Sample

To assess the significance of our findings with PAA, we conducted additional experiments with biologically-relevant molecules (albumin) and samples (plasma and blood). This appears to be particularly relevant given that in our previous study [22], we found that GCMS analyses of plasma samples, for which albumin is the predominant proteins, resulted in a predominant signal at m/z 257; there was little if any signal at m/z 258. Results from the present study raised the possibility that the GCMS signal at m/z 257 may arise from HNE bound to lysine and/or histidine residues of circulating proteins.

Incubations of Albumin with HNE.

Figure 16:
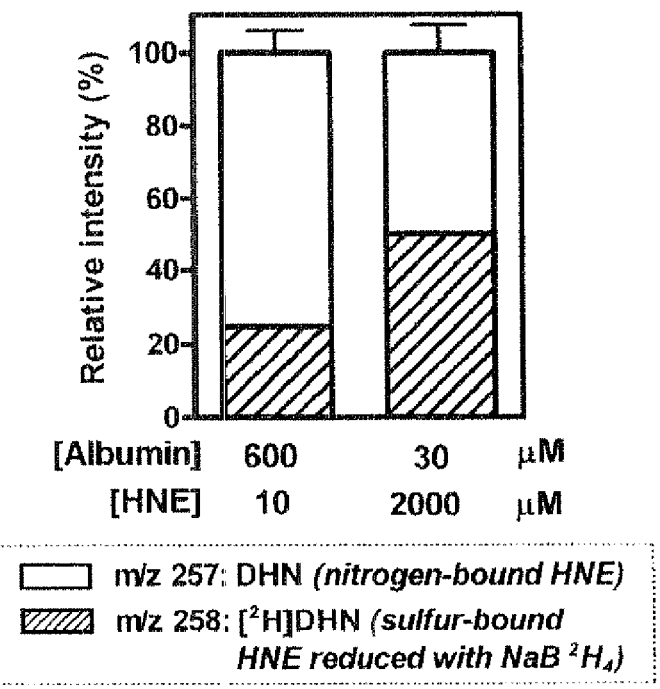
FIG. 16, in a bar chart, illustrates GCMS analysis of solutions of albumin incubated with HNE. Bovine serum albumin (50 or 600 µM) was incubated with HNE (10 µM to 2 mM) in 50 mM sodium phosphate buffer, pH 7.4 at 37° C. under various conditions and the reaction mixture was dialysed as described for PAA incubation mixtures in the Methods. GCMS data are corrected for natural abundance in heavy isotopes and expressed as % of the total GCMS signal intensity at ions m/z 257 and 258. Values are means±SD of 6 conditions conducted in triplicate determinations (600 µM albumin+10 µM) or 2 experiments (50 µM albumin+2 mM HNE). The origin of the signal at ions m/z 257 and 258 is indicated in parenthesis.

Incubation of 10 µM HNE with 600 µM albumin, which is similar to conditions described by Aldini et al. [29] and equivalent to concentrations found in plasma, resulted in a predominant GCMS signal at m/z 258 corresponding to [²H]DHN (75%: Structure A, FIG. 10) irrespective of incubation time (1-15 h) and HNE concentration (10 µM-2 mM; FIG. 16). However, when the concentration of albumin in the incubation mixture was decreased 20-fold, thus increasing the ratio HNE-to-albumin from 1/60 (600 µM albumin+10 µM HNE) to 60 (30 µM albumin+2 mM HNE), similar to conditions used by Szapacs et al. [30], the GCMS signal at m/z 257 was increased from 25 to 50% suggesting increasing binding of HNE through nitrogen-based residues, most likely histidine or lysine residues (FIG. 16). Together these results emphasize the importance of the ratio albumin-to-HNE as a factor determining the proportion of HNE bound to cysteine versus histidine and lysine residues to albumin molecules.

DNPH to Discriminate Between Various HNE-P Molecular Species in Blood and Plasma Samples.

Figure 14:
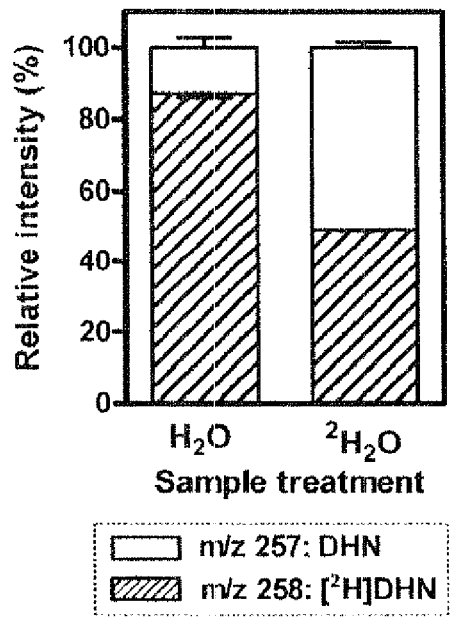
FIG. 14, in a bar chart, illustrates GCMS analysis of samples from incubations of poly-L-lysine and HNE treated with Raney nickel in H₂O and ²H₂O. Incubation conditions and sample processing were as described for FIG. 12 except that at the Raney nickel step, samples were dissolved either in H2O or ²H₂O. GCMS data are corrected for natural abundance in heavy isotopes and expressed as % of the total GCMS signal intensity at ions m/z 257 and 258. Values are means±SD of two experiments conducted in 3-5 replicate determinations (CV<10%). Note the increase in signal intensity at m/z 258 for samples treated with ²H₂O.

In order to assess the proportion of HNE bound to circulating proteins via cysteine vs. lysine and/or histidine residues, we have first treated parallel plasma samples with Raney nickel in the presence of $H_2O$ and $^2H_2O$, respectively, based on the observed selective reactivity of HNE bound to PAA containing cysteine, lysine or histidine residues to these two treatments (see FIG. 14). As shown in FIG. 17, treatment of plasma samples with Raney nickel in the presence of $^2H_2O$ resulted in a shift in the intensity of the GCMS signal observed at m/z 257 (~25% decrease) to m/z 258, which suggested the presence of HNE bound to histidine and/or lysine residues. However, the partial shift of the GCMS signal at m/z 257 raised the possibility of an incomplete deuterium exchange. An alternative explanation would be that plasma samples contain also protein adducts consisting of DHN covalently linked to cysteine residues, which may arise from the reduction of the free carbonyl group of HNE bound to proteins via thioether linkages to an alcohol group by aldose reductase [31].

Thus, we tested the capacity of DNPH, which reacts readily with the carbonyl group of aldehydes, to discriminate between HNE-P via cysteine vs. histidine and/or lysine residues, as well as protein-bound DHN (DHN-P). We reasoned that DNPH will react with the free carbonyl group of HNE bound to proteins via either cysteine, histidine or lysine residues to form an imine, which would be subsequently reduced to a secondary amine by $NaB^2H_4$.

Figure 18:
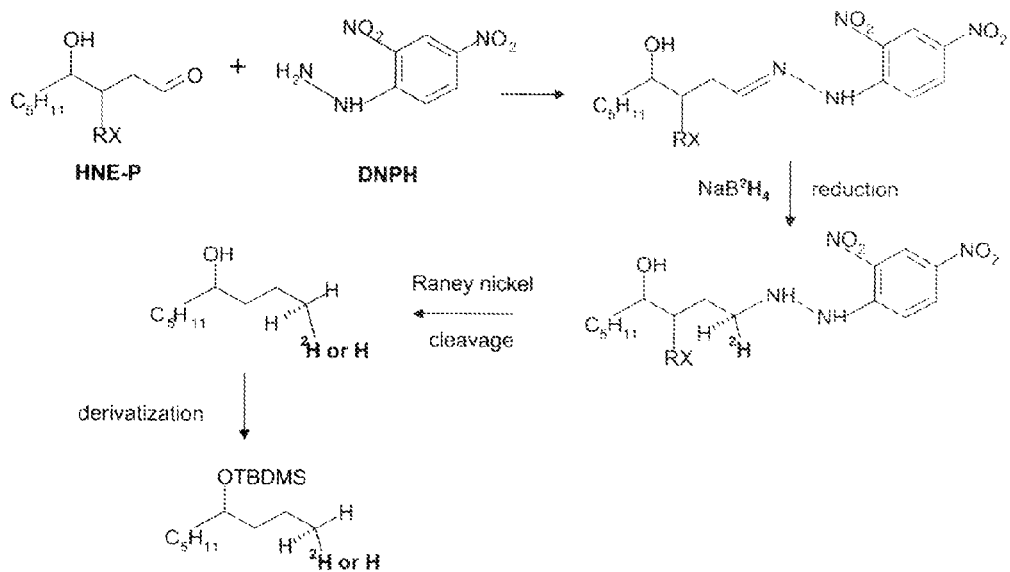
FIG. 18, in a schematic view, illustrates an overview of the experimental strategy to quantify sulfur and nitrogen-bound HNE via Michael adducts using diphenylhydrazine (DNPH). DNPH reacts with the free carbonyl group of HNE bound to protein via either cysteine, histidine or lysine residues to form an imine, which is subsequently reduced to a secondary amine by NaB2H4. Following Raney nickel treatment, the C—N bond will be cleaved, releasing unlabeled or [2H]labeled 4-hydroxynonane, which upon derivatization will form a mono-TBDMS derivative.

Following Raney nickel treatment, the C—N bond will be cleaved, releasing unlabeled or [²H]labeled 4-hydroxynonane, which upon derivatization will form a mono-TBDMS derivative (FIG. 18). The latter derivative cannot be detected using the GCMS conditions selected for the di-TBDMS derivative of DHN (shown in FIG. 10). However, DHN-P will not be modified by DNPH treatment and following Raney nickel treatment, these adducts will release unlabeled DNH, which will be converted to a di-TBDMS derivative, yielding a GCMS signal at m/z 257 (FIG. 10, structure B).

The aforementioned DNPH-based approach was first tested using standard solutions of HNE and DHN. This yielded the expected results that is a GCMS signal corresponding to DHN (m/z 257), but resulted in the complete abrogation of the signal corresponding to HNE (m/z 258) (data not shown). Then, we conducted a calibration curve in plasma samples similar to that reported in our previous publication (see FIG. 12 in Ref. [22]) to test the linearity of GCMS signal response at m/z 257 in the presence of DNPH. As shown in FIG. 19, the GCMS signal intensity at m/z 257 in plasma treated with DNPH, which was ~50% lower than that of untreated samples, displayed a linear relationship with sample volume between 200 and 500 µL (FIG. 19); the positive value at the y-intercept indicates a constant bias similar to that previously described [22]. It is noteworthy that treatment of samples with $NaB^2H_4$ following DNPH addition did not modify the results.

Finally, FIG. 20 reports quantitative values for the various HNE-P species, including DHN-P for whole blood and plasma collected from normal 22-wk-old Wistar rats. A GCMS signal at m/z 258, corresponding to [²H]DHN released from HNE-P via cysteine residues, was detected exclusively in whole blood samples and evaluated at 0.75±0.12 µmol/mg proteins in agreement with our previous study [22]. As expected, this signal was completely abolished by DNPH treatment (FIG. 20, panel A). In contrast, the strong GCMS signal at m/z 257 in whole blood was not affected by DNPH treatment (FIG. 20, panel B), indicating the presence of DHN-P, whose level is evaluated at 1.59±0.02 pmol/mg proteins. Conversely, in plasma, DNPH treatment decreased by ~60% the intensity of the GCMS signal at m/z 257 (FIG. 20, panel D): the difference in signal intensity in the absence and in the presence of DNPH is attributed to HNE-P via nitrogen residues (1.71±0.31 pmol/mg proteins), while the remaining signal in the presence of DNPH is attributed to DHN-P (1.14±0.15 pmol/mg proteins).

Discussion (Example 6)

Nature of HNE-Protein Adducts Detected by GCMS Assay Following Raney Nickel Treatment The ability of Raney nickel to cleave thioether bonds is well known and has been applied to measurement of HNE bound to glutathione and protein thiols [25]. Our results obtained from incubations of poly-L-cysteine-L-glutamate with HNE have confirmed this notion as evidenced by a predominant GCMS signal at m/z 258 (FIG. 11), which corresponds to [²H]DHN(HNE reduced with $NaB^2H_4$) released following treatment of incubation solutions with Raney nickel. In contrast, to the best of our knowledge, the possibility of carbon-nitrogen cleavage with Raney nickel has only been reported by Keefer and Lunn [26], although this was not specifically examined for HNE-P. In the present study, we have tested this possibility using HNE incubated with poly-L-lysine and poly-L-histidine. The GCMS analysis of samples from incubations of poly-L-lysine (FIG. 12, panel A) or poly-L-histidine (FIG. 12, panel B) with HNE exhibited a predominant GCMS signal at m/z 257 corresponding to unlabeled DHN (FIG. 10, structure A) rather than the expected signal at m/z 258 corresponding to [2H]DHN (FIG. 10, structure B). Furthermore the incubations with poly-L-lysine or poly-L-histidine and [2H3]HNE have lead to a GCMS signal that was increased by 3 mass units (FIG. 13, panels A-B).

Figure 13:
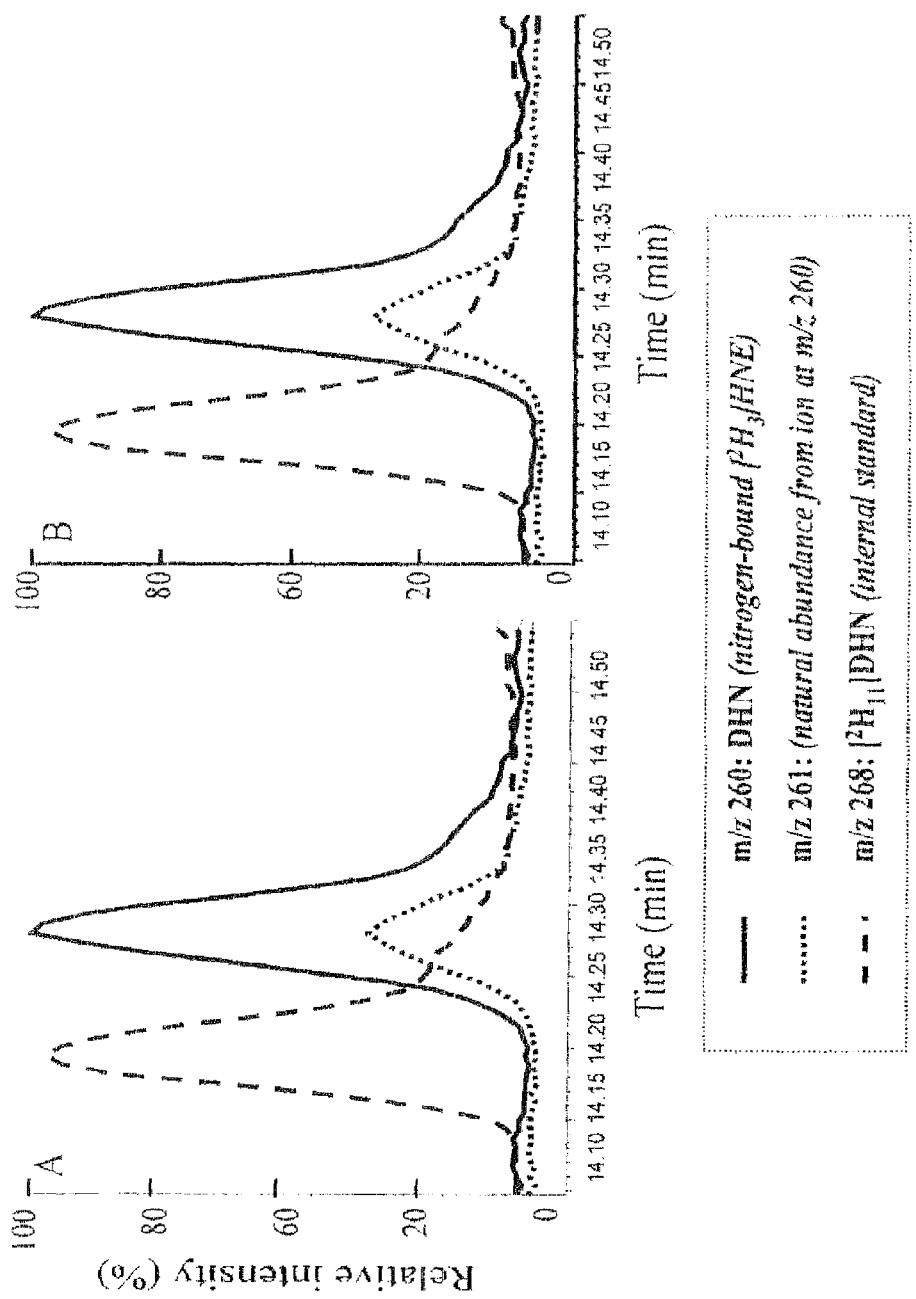
FIG. 13, in X-Y graphs, illustrates representative selected ion chromatograms of samples from incubations of poly-L-lysine (A) or poly-L-histidine (B) with [²H₃]HNE. Incubation conditions and sample processing were as described for FIG. 12 except that HNE was replaced by [²H₃]HNE. The origin of the signal at the various ions is indicated in parentheses.

From these results, we concluded that the ions at m/z 257 and 258 in FIG. 12, panel A-B, but at m/z 260 and 261 in FIG. 13, panels A-B had to come from unlabeled or [$^2$H3]labeled HNE, respectively. Additional data supporting the notion that our GCMS method detects nitrogen-bound HNE is provided by our finding that our GCMS data concur with those obtained from the analysis of incubations PAA/HNE mixtures with the protein carbonyl assay (Table 1). Indeed, the order of reactivity of the various amino acids with HNE determined with GCMS or protein carbonyl is similar and consistent with literature results: cysteine>>histidine>lysine>>arginine [5]. It is usually considered that cysteine is the most reactive amino acid towards HNE, while HNE adducts of histidine are more stable than either cysteine or lysine conjugates toward retro-Michael addition [5,32-34]. The very low levels of HNE found for poly-L-arginine and the absence of signal for poly-L-glutamate nor poly-L-serine is also consistent with the general reactivity of HNE toward amino acids. Nevertheless, there were some differences in the absolute quantity of HNE adducts evaluated by GCMS vs. DNPH, particularly for cysteine (6-fold greater) and histidine (1.6-fold lower), which may be explained by conditions used for sample processing and analyses, specifically NaB$^2$H$_4$ reduction of the reactive carbonyl group of HNE at 4° C. for GCMS vs. room temperature for the DNPH method.

Collectively, these data provide evidence that in addition to sulfur-bound HNE, Raney nickel treatment cleaves also nitrogen-bound HNE at 55° C. To the best of our knowledge, cleavage of the latter adducts with Raney nickel has not been previously documented. This may be due to variations in the catalytic strength of the Raney nickel preparations or duration of treatment. Indeed, further supporting this notion is the fact that the GCMS signal observed required minimally 15 h of treatment with Raney nickel to reach a maximal value as opposed to 5 h for HNE adducts with cysteine. This is consistent with the binding energies of the carbon-nitrogen and carbon-sulfur bonds, which are 305 kJ/mol and 272 kJ/mol, respectively.

We reason that our method detects only Michael adducts and not Schiff bases. Specifically, HNE released from Schiff bases using Raney nickel is expected to form a mono-TB-DMS derivative of 4-hydroxynonane, which would not be detected under the GCMS conditions (i.e. retention time and ions monitored) selected for the di-TBDMS derivative of DHN that is formed with Michael HNE-protein adducts (FIG. 10) because it would elute at an earlier time [28]. Additionally, when the temperature of the MS source is set at 150° C., it is possible to analyze and quantify the TBDMS derivatives of DHN and [$^2$H]DHN at m/z 389 and 390, respectively, which correspond to the molecular ion (no loss of [OTB-DMS] group as shown in FIG. 10) rather than at m/z 257 and 258. In previous studies [22,23], we did not find any differences in the GCMS signals at these two ion sets further supporting the notion that we are detecting HNE released from Michael adducts. In fact, it is well established that Schiff bases are generated in lower amounts than Michael adducts with HNE, which is in contrast to 4-oxo-2-nonenal [35]. Furthermore, other authors were unable to detect any compound consistent with the predicted structure of the reduced Schiff-base adduct of HNE to lysine as detected by GCMS when HNE was incubated with Nα-(formyl)lysine after reduction and acid hydrolysis [21].

Based on the results of this study and literature data [29, 30,36], we also reasoned that the protein amino acid residues that bind HNE through a carbon-nitrogen linkage are likely to be histidine and/or lysine. Most likely, our method detects all histidine-bound HNE, since these are exclusively Michael-type adducts. However, lysine residues can react with HNE to form both Michael adducts (for e.g. albumin lysine residues 199 and 525) and Schiff bases (albumin lysine residues 195, 199 and 525) [36], which are not detected by our GCMS assay.

Differential Reactivity of Sulfur- and Nitrogen-Bound HNE to Treatment with NaB2H4 and Raney Nickel Replacing H$_2$O by $^2$H$_2$O during Raney nickel treatment of poly-L-lysine or poly-L-histidine, which had been incubated with HNE and reduced with NaB$^2$H$_4$, induced a shift in the MS signal from m/z 257 to m/z 258 corresponding to [$^2$H] DHN (FIG. 14). These data can be related to similar observations made with sugars under treatment with Raney nickel incubated in $^2$H$_2$O [37,38] which is known as the Koch-Stuart procedure. The authors describe deuterium-hydrogen exchange of hydrogen atoms that are bound to carbon atoms carrying free hydroxyl groups. This may also occur while reduced HNE is tied to the metal surface through the N atom, following the sequence of reactions proposed in FIG. 15. The longer residence time on the catalyst would explain our finding that the exchange occurs only for lysine and histidine, but not for cysteine.

Experiments with Biologically-Relevant Samples

Our results have shown that when the ratio HNE-to-albumin increase from 1/60 (600 µM albumin+10 µM HNE) to 60 (30 µM albumin+2 mM HNE), the GCMS signal at m/z 257 was doubled (FIG. 16). The former incubation conditions are similar to albumin concentration in plasma and HNE concentration during acute oxidative stress conditions and the corresponding results are consistent with the finding of Aldini et al. [29,36] that cysteine at position 34 of albumin is the most reactive site for binding of HNE, followed by lysine 1999 and histidine 146. However, the latter incubation conditions are similar to that used by Szapacs et al. [30] who found that HNE was adducted with histidine (H) and lysine (K) in this order of reactivity: H242>H510>H67>H367>H247>K233. Accordingly, our results concur with the notion that binding of HNE to histidine and/or lysine residues becomes more important when the HNE concentration is several-fold in excess over that of albumin. This may explain why in the recent study by Roe et al., histidine adducts predominated when 1 mg protein from yeast whole cell extracts was incubated with 250 µM to 5 mM HNE [39]. More importantly, results of this study substantiate the concentration and distribution of the various HNE-P species in blood and plasma samples using DNPH, a reagent that shows great reactivity towards carbonyl groups as illustrated in FIG. 9. Specifically, treatment of whole blood samples with excess DNPH abolished completely the signal at m/z 258 corresponding to [H2]DHN (arising from HNE bound to protein thiols treated with NaB2H4) (FIG. 11, panel A). In contrast, the signal observed at m/z 257 in plasma and whole blood samples was quenched differently by DNPH treatment. In fact, it was unaffected in whole blood (FIG. 11, panel B), indicating that it arises exclusively from DHN bound to protein thiols, but was decreased by ~60% in plasma (FIG. 11, panel D). This signal loss is attributed to HNE-P via nitrogen residues. Circulating levels of all these various adducts in plasma and blood ranged between 0.15 and 2.9 µmol/mg proteins, which is equivalent to 10 and 600 nM. These values are similar to those reported for HNE-modified albumin in human subjects using a specific monoclonal antibody against histidine-HNE adducts plus an antibody against human serum albumin (611 nM) [12], which implied that ~0.1% of circulating albumin was modified by HNE.

Our finding of a significant level of DHN-P both in plasma and blood raises the possibility that cysteine-bound HNE-P is detoxified to some extent in situ. Furthermore, the discrepancy between our findings with plasma proteins (almost exclusively nitrogen-bound HNE and cysteine-bound DHN), which consist predominantly of albumin, and those from in vitro incubations of physiological concentrations of albumin and HNE (80 and 20% of cysteine- and nitrogen-bound HNE, respectively) suggests the existence of enzymatic mechanism in situ (that are absent in the in vitro incubation) [40-43]. For example, erythrocytes are well known to efficiently metabolize free HNE to glutathione conjugates and 4-hydroxynonanoic acid [43], while aldose reductase has been shown to reduce glutathione23 bound HNE to 1,4-dihydroxy-2-nonene [31]. However, further investigations are needed to substantiate the detoxification role of this enzyme, particularly toward HNE-P.

CONCLUSION

Results from this study demonstrate that Raney nickel treatment not only cleaves Michael adducts of HNE with cysteine residues, but also nitrogen-bound HNE, most likely through histidine and lysine residues. More importantly, additional data demonstrate that the parallel processing of blood and plasma samples with or without DNPH combined with Raney nickel treatment enables to discriminate and quantify with precision the levels of these various HNEP species in blood and plasma samples, which amount to 0.15 to 2.9 nmol/mg proteins or 10-600 nM. This allows the production of a "signature" of HNE-cysteine adduct concentrations, which is potentially indicative of the various causes that resulted in the creation of the HNE-cysteine adducts Interestingly, we found that while normal rat blood samples contained cysteinebound HNE-P, significant levels of nitrogen-bound HNE-P were only detected in plasma.

Finally, our finding of a significant level of DHN-P in blood and plasma suggests the existence of a detoxification mechanism in situ for HNE-P. Additional investigations are needed to evaluate the impact of age and disease on the level of the various HNE-P molecular species as well as that of DHN-P.

Although the present invention has been described hereinabove by way of preferred embodiments thereof, it can be modified without departing from the spirit, scope and nature of the subject invention, as defined in the appended claims.

LIST OF REFERENCES

[1] Carini, M.; Aldini, G.; Facino, R. M. Mass spectrometry for detection of 4-hydroxytrans-2-nonenal (HNE) adducts with peptides and proteins. *Mass Spectrom. Rev.* 23:281-305; 2004.

[2] Uchida, K. Role of reactive aldehyde in cardiovascular diseases. *Free Radic. Biol. Med.* 28:1685-1696; 2000.

[3] Benedetti, A.; Comporti, M.; Esterbauer, H. Identification of 4-hydroxynonenal as acytotoxic product originating from the peroxidation of liver microsomal lipids. *Biochim. Biophys. Acta* 620:281-296; 1980.

[4] Mlakar, A.; Spiteller, G. Previously unknown aldehydic lipid peroxidation compounds of arachidonic acid. *Chem. Phys. Lipids* 79:47-53; 1996.

[5] Doorn, J. A.; Petersen, D. R. Covalent modification of amino acid nucleophiles by the lipid peroxidation products 4-hydroxy-2-nonenal and 4-oxo-2-nonenal. *Chem. Res. Toxicol.* 15:1445-1450; 2002.

[6] Benderdour, M.; Charron, G.; DeBlois, D.; Comte, B.; Des Rosiers, C. Cardiac mitochondrial NADP+-isocitrate dehydrogenase is inactivated through 4-hydroxynonenal adduct formation: an event that precedes hypertrophy development. *J. Biol. Chem.* 278:45154-45159; 2003.

[7] Grimsrud, P. A.; Picklo, M. J.; Sr., Griffin, T. J., Bernlohr, D. A. Carbonylation of adipose proteins in obesity and insulin resistance: identification of adipocyte fatty acid-binding protein as a cellular target of 4-hydroxynonenal. *Mol. Cell. Proteomics* 6: 624-637; (2007).

[8] Uchida, K. 4-Hydroxy-2-nonenal: a product and mediator of oxidative stress. *Prog. Lipid Res.* 42:318-343; 2003.

[9] Uchida, K.; Itakura, K.; Kawakishi, S.; Hiai, H.; Toyokuni, S.; Stadtman, E. R. Characterization of epitopes recognized by 4-hydroxy-2-nonenal specific antibodies. *Arch. Biochem. Biophys.* 324:241-248; 1995.

[10] Yoritaka, A.; Hattori, N.; Uchida, K.; Tanaka, M.; Stadtman, E. R.; Mizuno, Y. Immunohistochemical detection of 4-hydroxynonenal protein adducts in Parkinson disease. *Proc. Natl. Acad. Sci. U.S.A.* 93:2696-2701; 1996.

[11] Traverso, N.; Menini, S.; Cosso, L.; Odetti, P.; Albano, E.; Pronzato, M. A.; Marinari, U. Immunological evidence for increased oxidative stress in diabetic rats. *Diabetologia* 41:265-270; 1998.

[12] Moreaua, R.; Nguyena, B. T.; Doneanuc, C. E.; Hagena, T. M. Reversal by aminoguanidine of the age-related increase in glycoxidation and lipoxidation in the cardiovascular system of Fischer 344 rats. *Biochem. Pharmacol.* 69:29-40;

[13] Toyokuni, S.; Yamada, S.; Kashima, M.; Ihara, Y.; Yamada, Y.; Tanaka, T.; Hiai, H.; Seino, Y.; Uchida, K. Serum 4-hydroxy-2-nonenal-modified albumin is elevated in patients with type 2 diabetes mellitus. *Antioxid. Redox Signal.* 2:681-685; 2000.

[14] Kimura, H.; Liu, S.; Yamada, S.; Uchida, K.; Matsumoto, K.; Mukaida, M.; Yoshida, K. Rapid increase in serum lipid peroxide 4-hydroxynonenal (HNE) through monocyte NADPH oxidase in early endo-toxemia. *Free Radic. Res.* 39:845-851; 2005.

[15] Alderton, A. L.; Faustman, C.; Liebler, D. C.; Hill, D. W. Induction of redox instability of bovine myoglobin by adduction with 4-hydroxy-2-nonenal. *Biochemistry* 42:4398-4405; 2003.

[16] Orioli, M.; Aldini, G.; Beretta, G.; Facino, R. M.; Carini, M. LC-ESI-MS/MS determination of 4-hydroxy-trans-2-nonenal Michael adducts with cysteine and histidine-containing peptides as early markers of oxidative stress in excitable tissues. *J Chromatogr B.* 827:109-118; 2005.

[17] Han, B.; Stevens, J. F.; Maier, C. S. Design, synthesis, and application of a hydrazidefunctionalized isotope-coded affinity tag for the quantification of oxylipid-protein conjugates. *Anal. Chem.* 79:3342-3354; 2007.

[18] Grimsrud, P. A.; Xie, H.; Griffin, T. J.; Bernlohr, D. A. Oxidative stress and covalent modification of protein with bioactive aldehydes. *J. Biol. Chem.* 283:21837-41; 2008.

[19] Selley, M. L. Determination of the lipid peroxidation product (E)-4-hydroxy-2-nonenal in clinical samples by gas chromatography—negative-ion chemical ionisation mass spectrometry of the O-pentafluorobenzyl oxime. *J. Chromatogr. B Biomed. Sci. Appl.* 691:263-268; 1997.

[20] Spies-Martin, D.; Sommerburg, O.; Langhans, C. D.; Leichsenring, M. Measurement of 4-hydroxynonenal in small volume blood plasma samples: modification of a gas chromatographic-mass spectrometric method for clinical settings. *J. Chromatogr. B Analyt. Technol. Biomed. Life Sci.* 774:231-239; 2002.

[21] Requena, J. R.; Fu, M. X.; Ahmed, M. U.; Jenkins, A. J.; Lyons, T. J.; Baynes, J. W.; Thorpe, S. R. Quantification of malondialdehyde and 4-hydroxynonenal adducts to lysine

[22] Asselin, C.; Bouchard, B.; Tardif, J. C.; Des Rosiers, C. Circulating 4-hydroxynonenalprotein thioether adducts assessed by gas chromatography-mass spectrometry are increased with disease progression and aging in spontaneously hypertensive rats. *Free Radic. Biol. Med.* 41:97-105; 2006.

[23] Veronneau, M.; Comte, B.; Des Rosiers, C. Quantitative gas chromatographic-mass spectrometric assay of 4-hydroxynonenal bound to thiol proteins in ischemic/reperfused rat hearts. *Free Radic. Biol. Med.* 33:1380-1388; 2002.

[24] Rilling, H. C.; Bruenger, E.; Epstein, W. W.; Kandutsch, A. A. Prenylated proteins: demonstration of a thioether linkage to cysteine of proteins. *Biochem. Biophys. Res. Commun.* 163:143-148; 1989.

[25] Uchida, K.; Stadtman, E. R. Selective cleavage of thioether linkage in proteins modified with 4-hydroxynonenal. *Proc. Natl. Acad. Sci. U.S. A* 89:5611-5615; 1992.

[26] Keefer, L. K.; Lunn, G. Nickel-Aluminum Alloy as a Reducing Agent. *Chem. Rev.* 89:459-502; 1989.

[27] Uchida, K.; Kanematsu, M.; Sakai, K.; Matsuda, T.; Hattori, N.; Mizuno, Y.; Suzuki, D.; Miyata, T.; Noguchi, N.; Niki, E.; Osawa, T. Protein-bound acrolein: potential markers for oxidative stress. *Proc. Natl. Acad. Sci. U.S.A.* 95:4882-4887; 1998.

[28] Des Rosiers, C.; Rivest, M. J.; Boily, M. J.; Jetté, M.; Carrobé-Cohen, A.; Kumar A. Gas chromatographic-mass spectrometric assay of tissue malondialdehyde, 4-hydroxynonenal, and other aldehydes after their reduction to stable alcohols. *Anal Biochem.* 208:161-170; 1993.

[29] Aldini, G.; Gamberoni, L.; Orioli, M.; Beretta, G.; Regazzoni, L.; Maffei, F. R.; Carini, M. Mass spectrometric characterization of covalent modification of human serum albumin by 4-hydroxy-trans-2-nonenal. *J. Mass Spectrom.* 41:1149-1161; 2006.

[30] Szapacs, M. E.; Riggins, J. N.; Zimmerman, L. J.; Liebler, D. C. Covalent adduction of human serum albumin by 4-hydroxy-2-nonenal: kinetic analysis of competing alkylation reactions. *Biochemistry.* 45:10521-10528; 2006.

[31] Oppermann, U. Carbonyl reductases: the complex relationships of mammalian carbonyl- and quinone-reducing enzymes and their role in physiology. *Annu. Rev. Pharmacol. Toxicol.* 47:293-322; 2007.

[32] Petersen, D. R.; Doorn, J. A. Reactions of 4-hydroxynonenal with proteins and cellular targets. Free Radic. Biol. Med. 37:937-945; 2004.

[33] Nadkarni, D. V.; Sayre, L. M. Structural definition of early lysine and histidine adduction chemistry of 4-hydroxynonenal. *Chem. Res. Toxicol.* 8:284-291, 1995.

[34] Petersen, D. R.; Doorn, J. A. Reactions of 4-hydroxynonenal with proteins and cellular targets. *Free Radic. Biol. Med.* 37:937-945, 2004.

[35] Sayre, L. M.; Lin, D.; Yuan, Q.; Zhu, X.; Tang, X. Protein adducts generated from products of lipid oxidation: focus on HNE and ONE. *Drug Metab Rev.* 38:651-675; 2006.

[36] Aldini, G.; Vistoli, G.; Regazzoni, L.; Gamberoni, L.; Facino, R. M.; Yamaguchi, S.; Uchida, K.; Carini, M. Albumin is the main nucleophilic target of human plasma: a protective role against pro-atherogenic electrophilic reactive carbonyl species? *Chem. Res. Toxicol.* 21:824-835; 2008.

[37] Angyal, S. J.; Stevens, J. D.; Odier, L. Selective deuteration over Raney nickel in deuterium oxide: 1,6-anhydrohexoses. *Carbohydr. Res.* 169:151-157; 1987.

[38] Djedaini, F.; Desalos, J.; Perly, B. Regio- and stereoselective deuterium labelling of β-cyclodextrin. *J. Labeled Comp. Radiopharm.* 28:785-791; 1990.

[39] Roe, M. R.; Xie, H.; Bandhakavi, S.; Griffin, T. J. Proteomic Mapping of 4-Hydroxynonenal Protein Modification Sites by Solid-Phase Hydrazide Chemistry and Mass Spectrometry. *Anal. Chem.* 79: 3747-3756; 2007.

[40] Ohara, H., Miyabe, Y., Deyashiki, Y., Matsuura, K., Hara, A. Reduction of drug ketones by dihydrodiol dehydrogenases, carbonyl reductase and aldehyde reductase of human liver. *Biochem. Pharmacol.* 50:221-227; 1995.

[41] O'Connor, T.; Ireland, L. S.; Harrison, D. J.; Hayes, J. D. Major differences exist in the function and tissue-specific expression of human aflatoxin B1 aldehyde reductase and the principal human aldo-keto reductase AKR1 family members. *Biochem. J.* 343:487-504; 1999.

[42] Luckey, S. W.; Petersen, D. R. Metabolism of 4-hydroxynonenal by rat Kupfer cells. *Arch Biochem Biophys* 389: 77-83; 2001.

[43] Srivastava, S.; Dixit, B. L.; Cai, J.; Sharma, S.; Hurst, H. E.; Bhatnagar, A.; Srivastava, S. K. Metabolism of lipid peroxidation product, 4-hydroxynonenal (HNE) in rat erythrocytes: role of aldose reductase. *Free Radic. Biol. Med.* 29:642-651; 2000.

[1A] Veronneau, M.; Comte, B.; Des Rosiers C. Quantitative gas chromatographic-mass spectrometric assay of 4-hydroxynonenal bound to thiol proteins in ischemic/reperfused rat hearts. Free Radic. Biol. Med 33:1380-1388; 2002.

[2A] Cabassi, A.; Dumont, E. C.; Girouard, H.; Bouchard, J. F.; Le Jossec, M.; Lamontagne, D.; Besner, J. G.; de Champlain, J. Effects of chronic N-acetylcysteine treatment on the actions of peroxynitrite on aortic vascular reactivity in hypertensive rats. J. Hypertens. 19:1233-1244; 2001.

[3A] Yuan, Y. V.; Kitts, D. D. Dietary (n-3) fat and cholesterol alter tissue antioxidant enzymes and susceptibility to oxidation in SHR and WKY rats. J. Nutr. 133:679-688; 2003.

[4A] Kobayashi, N.; DeLano, F. A.; Schmid-Schonbein, G. W. Oxidative stress promotes endothelial cell apoptosis and loss of microvessels in the spontaneously hypertensive rats. Arterioscler. Thromb. Vasc. Biol. 25:2114-2121; 2005.

[5A] Wang, X.; Desai, K.; Chang, T.; Wu, L. Vascular methylglyoxal metabolism and the development of hypertension. J. Hypertens. 23:1565-1573; 2005.

[6A] Cosentino, F.; Patton, S.; d'Uscio, L. V.; Werner, E. R.; Werner-Felmayer, G.; Moreau, P.; Malinski, T.; Luscher, T. F. Tetrahydrobiopterin alters superoxide and nitric oxide release in prehypertensive rats. J. Clin. Invest 101:1530-1537; 1998.

[7A] Benderdour, M.; Charron, G.; Comte, B.; Ayoub, R.; Beaudry, D.; Foisy, S.; Deblois, D.; Des Rosiers C. Decreased cardiac mitochondrial NADP+-isocitrate dehydrogenase activity and expression: a marker of oxidative stress in hypertrophy development. Am. J. Physiol Heart Circ. Physiol 287:H2122-H2131; 2004.

[8A] Des Rosiers C.; Rivest, M. J.; Boily, M. J.; Jette, M.; Carrobe-Cohen, A.; Kumar, A. Gas chromatographic-mass spectrometric assay of tissue malondialdehyde, 4-hydroxynonenal, and other aldehydes after their reduction to stable alcohols. Anal. Biochem. 208:161-170; 1993.

[9A] Morrow, J. D. The isoprostanes: their quantification as an index of oxidant stress status in vivo. Drug Metab Rev. 32:377-385; 2000.

[10A] Tsikas, D.; Schwedhelm, E.; Stutzer, F. K.; Gutzki, F. M.; Rode, I.; Mehls, C.; Frolich, J. C. Accurate quantification of basal plasma levels of 3-nitrotyrosine and 3-nitrotyrosinoalbumin by gas chromatography-tandem mass spectrometry. J. Chromatogr. B Analyt. Technol. Biomed. Life Sci. 784:77-90; 2003.

[11A] Strohmaier, H.; Hinghofer-Szalkay, H.; Schaur, R. J. Detection of 4-hydroxynonenal (HNE) as a physiological component in human plasma. J. Lipid Mediat. Cell Signal. 11:51-61; 1995.

[12A] Spies-Martin, D.; Sommerburg, O.; Langhans, C. D.; Leichsenring, M. Measurement of 4-hydroxynonenal in small volume blood plasma samples: modification of a gas chromatographic-mass spectrometric method for clinical settings. J. Chromatogr. B Analyt. Technol. Biomed. Life Sci. 774:231-239; 2002.

[13A] Kinter, M.; Robinson, C. S.; Grimminger, L. C.; Gillies, P. J.; Shimshick, E. J.; Ayers, C. Whole blood and plasma concentrations of 4-hydroxy-2-nonenal in Watanabe heritable hyperlipidemic versus New Zealand White rabbits. Biochem. Biophys. Res. Commun. 199: 671-675; 1994.

[14A] Oliver, C. N.; Ahn, B. W.; Moerman, E. J.; Goldstein, S.; Stadtman, E. R. Age-related changes in oxidized proteins. J. Biol. Chem. 262:5488-5491; 1987.

[15A] Schaur, R. J. Basic aspects of the biochemical reactivity of 4-hydroxynonenal. Mol. Aspects. Med 24:149-159; 2003.

[16A] Salomon, R. G.; Kaur, K.; Podrez, E.; Hoff, H. F.; Krushinsky, A. V.; Sayre, L. M. HNE-derived 2-pentylpyrroles are generated during oxidation of LDL, are more prevalent in blood plasma from patients with renal disease or atherosclerosis, and are present in atherosclerotic plaques. Chem. Res. Toxicol. 13:557-564; 2000.

[17A] Gillery, P.; Bordas-Fonfrede, M.; Chapelle, J. P.; Drouin, P.; Hue, G.; Levy-Marchal, C.; Perier, C.; Selam, J. L.; Slama, G.; Thivolet, C.; Vialettes, B. HBA1c: clinical and biological agreement for standardization of assay methods. Report by the experts of ALFEDIAM (Association de Langue Francaise pour (Etude du Diabete et des Maladies Metabolique) and SFBC (Societe Francaise de Biologie Clinique)). Diabetes Metab 25:283-287; 1999.

[18A] Selley, M. L. (E)-4-hydroxy-2-nonenal may be involved in the pathogenesis of Parkinson's disease. Free Radic. Biol. Med. 25:169-174; 1998.

[19A] Musiek, E. S.; Cha, J. K.; Yin, H.; Zackert, W. E.; Terry, E. S.; Porter, N. A.; Montine, T. J.; Morrow, J. D. Quantification of F-ring isoprostane-like compounds (F(4)-neuroprostanes) derived from docosahexaenoic acid in vivo in humans by a stable isotope dilution mass spectrometric assay. J. Chromatogr. B Analyt. Technol. Biomed. Life Sci. 799:95-102; 2004.

[20A] Nonaka-Sarukawa, M.; Yamamoto, K.; Aoki, H.; Takano, H.; Katsuki, T.; Ikeda, U.; Shimada, K. Increased urinary 15-F2t-isoprostane concentrations in patients with non-ischaemic congestive heart failure: a marker of oxidative stress. Heart 89:871-874; 2003.

[2A] Schwedhelm, E.; Bartling, A.; Lenzen, H.; Tsikas, D.; Maas, R.; Brummer, J.; Gutzki, F. M.; Berger, J.; Frolich, J. C.; Boger, R. H. Urinary 8-iso-prostaglandin F2alpha as a risk marker in patients with coronary heart disease: a matched case-control study. Circulation 109:843-848; 2004.

[22A] Gaut, J. P.; Byun, J.; Tran, H. D.; Heinecke, J. W. Artifact-free quantification of free 3-chlorotyrosine, 3-bromotyrosine, and 3-nitrotyrosine in human plasma by electron capture-negative chemical ionization gas chromatography mass spectrometry and liquid chromatography-electrospray ionization tandem mass spectrometry. Anal. Biochem. 300:252-259; 2002.

[23A] Shishehbor, M. H.; Aviles, R. J.; Brennan, M. L.; Fu, X.; Goormastic, M.; Pearce, G. L.; Gokce, N.; Keaney, J. F., Jr.; Penn, M. S.; Sprecher, D. L.; Vita, J. A.; Hazen, S. L. Association of nitrotyrosine levels with cardiovascular disease and modulation by statin therapy. JAMA 289:1675-1680; 2003.

[24A] Siems, W.; Grune, T. Intracellular metabolism of 4-hydroxynonenal. Mol. Aspects Med 24:167-175; 2003.

[25A] Doggrell, S. A.; Brown, L. Rat models of hypertension, cardiac hypertrophy and failure. Cardiovasc. Res. 39:89-105; 1998.

[26A] Shimamoto, N.; Goto, N.; Tanabe, M.; Imamoto, T.; Fujiwara, S.; Hirata, M. Myocardial energy metabolism in the hypertrophied hearts of spontaneously hypertensive rats. Basic Res. Cardiol. 77:359-7; 1982.

[27A] Diez, J.; Panizo, A.; Hernandez, M.; Vega, F.; Sola, I.; Fortuno, M. A.; Pardo, J. Cardiomyocyte apoptosis and cardiac angiotensin-converting enzyme in spontaneously hypertensive rats. Hypertension 30:1029-1034; 1997.

[28A] Reckelhoff, J. F.; Romero, J. C. Role of oxidative stress in angiotensin-induced hypertension. Am. J. Physiol Regul. Integr. Comp Physiol 284:R893-R912; 2003.

[29A] Poli, G.; Schaur, R. J. 4-Hydroxynonenal in the pathomechanisms of oxidative stress. IUBMB. Life 50:315-321; 2000.

[30A] Srivastava, S.; Dixit, B. L.; Cai, J.; Sharma, S.; Hurst, H. E.; Bhatnagar, A.; Srivastava, S. K. Metabolism of lipid peroxidation product, 4-hydroxynonenal (HNE) in rat erythrocytes: role of aldose reductase. Free Radic. Biol. Med. 29:642-651; 2000.

[31A] Asselin C, Bouchard B, Tardif J C, Des Rosiers C. Circulating 4-hydroxynonenal-protein thioether adducts assessed by gas chromatography-mass spectrometry are increased with disease progression and aging in spontaneously hypertensive rats. Free Radic Biol Med 2006; 41(1): 97-105.

32A] Benderdour M, Charron G, Deblois D, Comte B, Des Rosiers C. Cardiac mitochondrial NADP+-isocitrate dehydrogenase is inactivated through 4-hydroxynonenal adduct formation: an event that precedes hypertrophy development. J Biol Chem 2003; 278(46):45154-45159.

[33A] Benderdour M, Charron G, Comte B et al. Decreased cardiac mitochondrial NADP+-isocitrate dehydrogenase activity and expression: a marker of oxidative stress in hypertrophy development. Am J Physiol Heart Circ Physiol 2004; 287(5):H2122-H2131.

[34A] Chiappe De Cingolani G E, Caldiz C I. Insulin resistance and GLUT-4 glucose transporter in adipocytes from hypertensive rats. Metabolism 2004; 53(3):382-387.

[35A] Shimamoto N, Goto N, Tanabe M, Imamoto T, Fujiwara S, Hirata M. Myocardial energy metabolism in the hypertrophied hearts of spontaneously hypertensive rats. Basic Res Cardiol 1982; 77(4):359-7.

[36A] Cosentino F, Patton S, d'Uscio L V, Werner E R, Werner-Felmayer G, Moreau P et al. Tetrahydrobiopterin alters superoxide and nitric oxide release in prehypertensive rats. J Clin Invest 1998; 101(7):1530-1537.

[37A] Cabassi A, Dumont E C, Girouard H, Bouchard J F, Le Jossec M, Lamontagne D et al. Effects of chronic N-acetylcysteine treatment on the actions of peroxynitrite on aortic vascular reactivity in hypertensive rats. J Hypertens 2001; 19(7):1233-1244.

[38A] Tardif J C, Gregoire J, Schwartz L, et al, for the Canadian Antioxidant Restenosis Trial (CART-1) Investigators. Effects of AGI-1067 and Probucol after percutaneous coronary interventions. Circulation 2003; 107:552-558.

[39A] Kohno I, Honma H, Nakamura T, Tamura K. Comparison of blood pressure, heart rate and activity between normotensive and spontaneously-hypertensive rats. Chronobiologia 1994; 21(1-2):45-56.

[40A] Slama M, Ahn J, Varagic J, Susic D, Frohlich E D. Long-term left ventricular echocardiographic follow-up of SHR and WKY rats: effects of hypertension and age. Am J Physiol Heart Circ Physiol 2004; 286(1):H181-H185.

[41A] Diaz A, Bourassa M G, Guertin M C, Tardif J C. Long-term prognostic value of resting heart rate in patients with suspected or proven coronary artery disease. Eur Heart J 2005; 26(10):967-974.

[42A] Nakamura K, Kusano K F, Matsubara H et al. Relationship between oxidative stress and systolic dysfunction in patients with hypertrophic cardiomyopathy. J Card Fail 2005; 11(2):117-123.

[43A] Ishikawa T, Esterbauer H, Sies H. Role of cardiac glutathione transferase and of the glutathione S-conjugate export system in biotransformation of 4-hydroxynonenal in the heart. J Biol Chem 1986; 261(4):1576-1581.

[44A] Bhatnagar A. Electrophysiological effects of 4-hydroxynonenal, an aldehydic product of lipid peroxidation, on isolated rat ventricular myocytes. Circ Res 1995; 76(2):293-304.

[45A] Aberle N S, Picklo M J, Sr., Amarnath V, Ren J. Inhibition of cardiac myocyte contraction by 4-hydroxy-trans-2-nonenal. Cardiovasc Toxicol 2004; 4(1):21-28.

[46A] Ahn J, Varagic J, Slama M, Susic D, Frohlich E D. Cardiac structural and functional responses to salt loading in SHR. Am J Physiol Heart Circ Physiol 2004; 287(2):H767-H772.

[47A] Brilla C G, Matsubara L, Weber K T. Advanced hypertensive heart disease in spontaneously hypertensive rats. Lisinopril-mediated regression of myocardial fibrosis. Hypertension 1996; 28(2):269-275.

[48A] Gagnon C, Legault F, Geraldes P, Tanguay J F, Lambert C. Diverse effects of Ace inhibitors and angiotensin II receptor antagonists on prevention of cardiac hypertrophy and collagen distribution in spontaneously hypertensive rats. Int J Cardiol 2004; 97(3):373-381.

[49A] Nakamura R, Egashira K, Machida et al. Probucol attenuates left ventricular dysfunction and remodeling in tachycardia-induced heart failure: roles of oxidative stress and inflammation. Circulation 2002; 106(3):362-367.

[50A] Poli G, Schaur R J. 4-Hydroxynonenal in the pathomechanisms of oxidative stress. IUBMB Life 2000; 50(4-5):315-321.

All references cited and/or discussed in this specification are incorporated herein by reference in their entirety and to the same extent as if each reference was individually incorporated by reference.

What is claimed is:

1. A method for detecting oxidative stress using a biological sample, comprising:
   (a) obtaining the biological sample comprising a biomarker of oxidative stress having a measurable component;
   (b) chemically stabilizing the biomarker in the sample;
   (c) isolating the measurable component;
   (d) extracting the measurable component; and
   (e) measuring the quantity of the measurable component.

2. A method as defined in claim 1, wherein the biomarker of oxidative stress is selected from an aldehyde-protein adduct and an aldehyde metabolite-protein adduct, said method further comprising measuring separately for the same protein biomarkers of oxydative stress formed with different amino acids of the protein.

* * * * *